(12) United States Patent
Skocic

(10) Patent No.: US 8,234,125 B2
(45) Date of Patent: Jul. 31, 2012

(54) HEALTH CARE DATA MANAGEMENT

(75) Inventor: Ruth E. Skocic, Garrettsville, OH (US)

(73) Assignee: MLP Technology, Inc., Ravenna, OH (US)

( * ) Notice: Subject to any disclaimer, the term of this patent is extended or adjusted under 35 U.S.C. 154(b) by 509 days.

(21) Appl. No.: 12/204,560

(22) Filed: Sep. 4, 2008

(65) Prior Publication Data

US 2009/0070148 A1  Mar. 12, 2009

Related U.S. Application Data

(63) Continuation-in-part of application No. 11/962,267, filed on Dec. 21, 2007, which is a continuation-in-part of application No. 11/592,913, filed on Nov. 6, 2006.

(60) Provisional application No. 60/876,048, filed on Dec. 21, 2006.

(51) Int. Cl.
*G06Q 10/00* (2012.01)
(52) U.S. Cl. ............ 705/2; 340/5.83; 600/529; 709/237
(58) Field of Classification Search ...... 705/2; 382/124; 709/237
See application file for complete search history.

(56) References Cited

U.S. PATENT DOCUMENTS

| | | | |
|---|---|---|---|
| 5,193,855 A | 3/1993 | Shamos | |
| 5,241,466 A | 8/1993 | Perry et al. | |
| 5,291,399 A | 3/1994 | Chaco | |
| 5,325,294 A | 6/1994 | Keene | |
| 5,499,293 A | 3/1996 | Behram | |
| 5,651,067 A | 7/1997 | Ahrens et al. | |
| 5,651,117 A | 7/1997 | Arbuckle | |
| 5,659,741 A | 8/1997 | Eberhardt | |
| 5,664,109 A | 9/1997 | Johnson et al. | |
| 6,031,910 A | 2/2000 | Deindl et al. | |
| 6,034,605 A | 3/2000 | March | |
| 6,126,204 A | 10/2000 | Arkinstall | |
| 6,845,448 B1 | 1/2005 | Chaganti et al. | |
| 7,039,628 B2 | 5/2006 | Logan, Jr. | |
| 7,102,516 B2 | 9/2006 | Orman | |
| 7,328,276 B2 * | 2/2008 | Alisuag | 709/237 |
| 7,542,912 B1 | 6/2009 | Durand | |
| 7,668,734 B2 * | 2/2010 | Pugh | 705/2 |
| 8,147,419 B2 * | 4/2012 | Krauss et al. | 600/529 |
| 2001/0044732 A1 * | 11/2001 | Maus et al. | 705/3 |
| 2002/0188473 A1 * | 12/2002 | Jackson | 705/2 |

(Continued)

FOREIGN PATENT DOCUMENTS

JP  9-231288  9/1997

OTHER PUBLICATIONS

Google patents search result.*

(Continued)

*Primary Examiner* — Dilek B Cobanoglu
(74) *Attorney, Agent, or Firm* — Merchant & Gould P.C.

(57) ABSTRACT

Health care data is stored in memory accessible to a server. The server allows users to access the health care data, such as across a communication network. In some embodiments a biometric identifier for a patient is stored with patient information. The biometric identifier can be used to control access to patient records and to quickly locate patient information associated with a particular patient.

11 Claims, 24 Drawing Sheets

U.S. PATENT DOCUMENTS

| | | | |
|---|---|---|---|
| 2003/0120515 | A1 | 6/2003 | Geller |
| 2003/0233254 | A1* | 12/2003 | Hamilton et al. .................. 705/2 |
| 2005/0240613 | A1 | 10/2005 | Logan, Jr. |
| 2006/0080151 | A1 | 4/2006 | Barbash |
| 2006/0085226 | A1* | 4/2006 | Kamber ............................. 705/2 |
| 2006/0229919 | A1 | 10/2006 | Pugh |
| 2007/0279187 | A1* | 12/2007 | Hekmatpour et al. ....... 340/5.83 |
| 2007/0292006 | A1* | 12/2007 | Johnson ......................... 382/124 |
| 2008/0114618 | A1 | 5/2008 | Pysnik et al. |

OTHER PUBLICATIONS

Google patents search, May 30, 2012.*

STIC NPL search report, Jun. 12, 2012.*

Landry FJ, Kroenke K., Lucas C. et al., Seminars on advance directives for adult outpatients increased completion rates; 1997; 1 page.

Landry FJ, Kroenke K., Lucas C., et al.; Seminars on advance directives for adult outpatients increased completion rates; Evidence-Based Nursing; 1998; 2 pages.

Google Search Results for advance directives seminars; 2 pages.

U.S. Appl. No. 11/962,267, filed Dec. 21, 2007, 22 pages.

U.S. Appl. No. 11/592,913, filed Nov. 6, 2006, 26 pages.

International Search Report and Written Opinion mailed Apr. 20, 2010.

* cited by examiner

HEALTH CARE DATA MANAGEMENT

CROSS REFERENCE TO RELATED APPLICATIONS

This application is a Continuation-In-Part of U.S. application Ser. No. 11/962,267 filed on Dec. 21, 2007, entitled MOBILE FINGERPRINT UNIT, which claims priority to U.S. Provisional Application Ser. No. 60/876,048, filed on Dec. 21, 2006, entitled MOBILE FINGERPRINT UNIT, the disclosure of which is incorporated by reference herein in its entirety.

This application is also a Continuation-In-Part of U.S. application Ser. No. 11/592,913 filed on Nov. 6, 2006, entitled METHOD OF COLLECTING AND TRANSMITTING ADVANCE DIRECTIVES DOCUMENTATION, the disclosure of which is incorporated by reference herein in its entirety.

BACKGROUND

Health care records are often maintained by a patient's primary caregiver. Perhaps the most common health care record is a medical record folder that contains documents describing the medical history of a patient. The documents often record information such as prescription drug prescriptions, immunization records, allergies, physician notes, and other information about the medical history of the patient.

When a medical event occurs, however, such medical records are often unavailable to a caregiver. For example, if a medical emergency occurs, an emergency medical technician (EMT) is often the first to arrive at the scene of the emergency. Since the EMT is typically not the primary caregiver and does not have access to the health care records, the EMT is not able to make use of the information in the health care record. In some instances, the patient is incapacitated and unable to provide the caregiver with such information. Further, if the patient is transferred to a hospital for further treatment, the health care records may still not be available, or at least not for a period of time.

Further, even if a health care record is available to a caregiver, the health care record is typically limited to information provided by the physician, and does not include the preferences or desires of the patient. A caregiver often relies upon information provided by the patient to match a health care record with the patient. Information such as name and birth date are often used, for example. However, this information is often publicly known and errors can occur in matching a health care record with a patient.

SUMMARY

In general terms, this disclosure is directed to health care data management. In one possible configuration and by non-limiting example, patient information including health information is associated with a biometric identifier of a patient. The biometric identifier is used to access the patient information.

One aspect is a health care data management system comprising a server device including a processor and memory. The memory contains a database and instructions executable by the processor to perform a method of managing health care data. The method includes: registering a user by receiving user data including a first biometric identifier; storing the user data and the first biometric identifier in the database and associating the first biometric identifier with the user data in the database; receiving health care information pertaining to the user and storing in the user data in the database; receiving from a caregiver computing system a request including a second biometric identifier; searching the database to identify the first biometric identifier as a match to the second biometric identifier; and transmitting at least part of the user data associated with the first biometric identifier to the caregiver computing system in response to the request.

Another aspect is a method of graphically presenting health information relating to a patient. The method comprises: displaying a graphical representation of at least a portion of a human body of the patient including a first body part; displaying a health flag associated with the first body part of the patient; receiving an input from a user identifying the first body part; and displaying at least part of a health history associated with the first body part.

Yet another aspect is a method of notifying a first person about the occurrence of an event pertaining to a registered user. The method comprises: registering a user as a registered user in a database by storing user data including a name and a biometric identifier associated with the registered user in the database; storing contact information into the user data, the contact information identifying a manner of communicating with the first user; identifying the occurrence of a health event associated with the registered user; and communicating with the first user according to the identified manner of communicating to inform the first user that the user data has been accessed by a caregiver.

BRIEF DESCRIPTION OF THE DRAWINGS

FIG. 11 is screen shot of an exemplary power of attorney interface according to the present disclosure.

FIG. 14 is a screen shot of an exemplary client profile interface according to the present disclosure.

DETAILED DESCRIPTION

Figure 1:
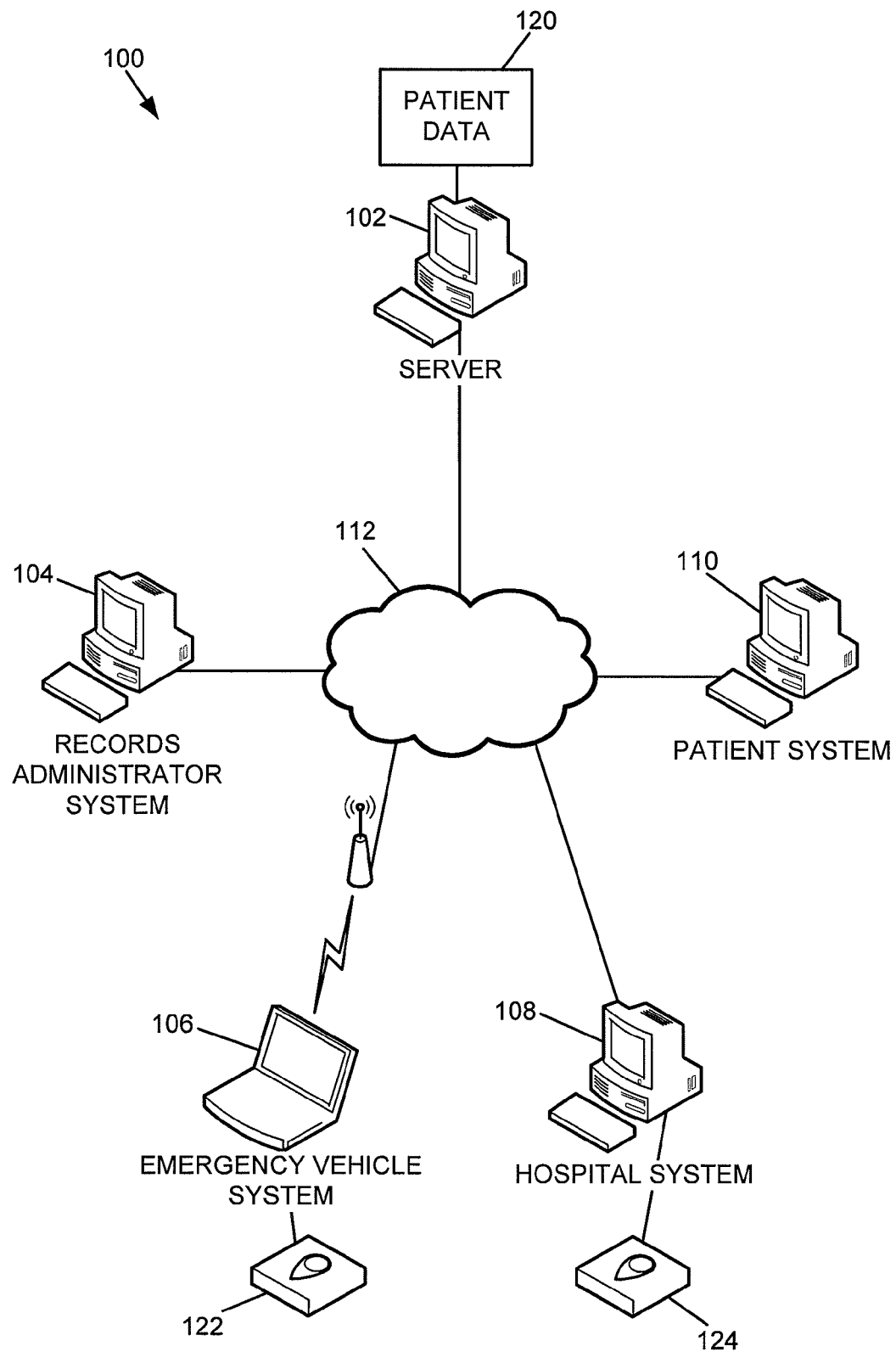
FIG. 1 is a schematic block diagram of an exemplary health care data management system according to the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The logical operations of the various embodiments of the invention described herein are implemented as: (1) a sequence of computer implemented operations running on a computing device; and/or (2) interconnected machine modules within the computing device. Modules represent functions executed by program code such as commonly available programming languages. The implementation used is a matter of choice dependent on the performance requirements of the particular programmable device, and associated computing devices. Accordingly, the logical operations making up the embodiments of the invention described herein can be referred to alternatively as operations, modules, and the like.

FIG. 1 is schematic block diagram of an exemplary health care data management system 100. System 100 includes server 102, records administrator computing system 104, emergency vehicle computing system 106, hospital computing system 108, and patient computing system 110. In some embodiments communication occurs across network 112. Server 102 includes patient data 120. Biometric readers 122 and 124 are coupled to emergency vehicle computing system 106 and hospital computing system 108.

Briefly, some embodiments of heath care data management system 100 operate to provide quick and convenient access to patient data 120, while protecting the privacy of patient data 120 from unauthorized access. For example, health records of a person (generally referred to as a "patient" herein) are stored in patient data 120 of server 102. If the person is involved in an emergency situation, emergency caregivers arrive on the scene with emergency vehicle computing system 106. A biometric reader 122 is used to read a biometric identifier of the patient (such as the patient's fingerprint). The health records associated with the patient's fingerprint are then obtained from server 102. As a result, the emergency caregivers are able to positively identify the patient (particularly if the patient is unable to identify herself) and review the health records of the patient immediately (in "real-time") to assist them in providing proper medical care to the patient. Similarly, when the patient enters the hospital, the biometric identifier of the patient is read with biometric reader 124 to provide access to the patient's medical records. Other embodiments are also described herein.

Some embodiments of health care data management system 100 include some or all of the following.

Server 102 is a computing system that stores or is able to access patient data 120. Server 102 is in data communication with network 112. In some embodiments server 102 is a Web server that generates data for one or more web pages. The data is communicated across network 112 to a computing system operating a browser software application. An example of server 102 is described with reference to FIG. 2.

In some embodiments server 102 stores patient data 120 in memory of server 102. In other embodiments, patient data 120 is stored remotely from server 102, but is accessible to server 102, such as across network 112 or another network. In some embodiments patient data 120 is stored in a database or other data record.

Patient data 120 includes information relating to a particular patient. Examples of patient data include medical history data (including physician notes, electronic medical records, immunization records, surgical history, medication records, medical treatment records, identification of medical allergies, obstetric history, habit history such as a history of smoking or alcohol abuse, and family medical history), mental health history, social history (including employment history, travel history, family history, and common activities), patient instructions (advance directive, living will, power of attorney for health care), and other data relating to the patient. Due to the confidential nature of patient data 120, measures are taken to carefully safeguard patient data 120 against unauthorized or improper use. For example, in some embodiments patient data 120 is Protected Health Information (PHI) that is managed in compliance with Health Insurance Portability and Accountability Act (HIPAA) standards. Other embodiments conform to other standards, such as one or more ISO standards. In some embodiments, communication of patient data 120 is performed in accordance with a secure data communication protocol, such as Secure Sockets Layer (SSL).

Records administrator system 104 is a computing system that operates to allow an administrator to oversee the administration of patient data on server 102. In some embodiments system 104 is the same as server 102, but typically system 104 is a separate computing system. Records administrator system 104 is typically operated by person performing as a records administrator.

Emergency vehicle computing system 106 is a computing system associated with an emergency vehicle, such as an ambulance or other emergency response unit. In some embodiments, emergency vehicle computing system 106 communicates wirelessly with network 112. Emergency vehicle computing system 106 is typically operated by a caregiver that provides health care from the emergency vehicle, such as an EMT. Other embodiments are used by other emergency responders, such as the police, FBI, and military units. The emergency vehicle computing system 106 accesses patient data 120 from server 102 in some embodiments. Examples of emergency vehicle computing systems 106 include a laptop computer, a handheld computing system, a tablet computer, a personal digital assistant (PDA), a cell phone, and other computing systems. In some embodiments emergency vehicle computing system 106 is a remote mobile computing system.

In some embodiments, emergency vehicle computing system 106 includes a wireless communication device. Examples of wireless communication devices include a radio transceiver, cell phone, wireless modem, satellite communication system, infrared communication system, and other communication systems that communicate using electromagnetic waves.

In some embodiments, emergency vehicle computing system 106 includes a biometric reader 122. The biometric reader 122 is configured to read a biometric identifier of a patient or caregiver. An example of a biometric reader is a fingerprint scanner. One example of a fingerprint scanner is the U.are.U Fingerprint Reader available from DigitalPersona, Inc. of Redwood City, Calif. Another example of a biometric reader includes a charge coupled device (CCD) for obtaining a digital image of a face, fingerprint, hand, or eye. Other biometric readers are used in other embodiments, such as a voice recognition system, laser, blood analyzer, pulse detector, or keystroke recognition system. In some embodiments multiple biometric readers are used.

Rather than, or in addition to, using a biometric reader, some embodiments include an alternate patient or user identifier. An example of a user identifier is a credit-card type device storing one or more unique identifiers, such as encoding a unique identification number in a magnetic stripe. The credit card can be swiped through a card reader to read the unique identifier. Other identifiers and readers are used in other embodiments, such as a magnetic card and card reader, RFID tag and detector, and the like.

Hospital computing system 108 is a computing system located in a caregiving facility, such as a hospital or other caregiver facility. Hospital computing system 108 is in data communication with network 112. Hospital computing system 108 is typically operated by a caregiver or employee of a caregiving facility.

In some embodiments, hospital computing system 108 also includes a biometric reader 124, similar to biometric reader 122 discussed above.

Patient computing system 110 is a computing system typically operated by patient, such as at the patient's home or office. However, in some embodiments patient computing system 110 is a mobile device, such as a laptop computer, cell phone, personal digital assistant, or other computing systems. In some embodiments patient computing system 110 operates to communicate data across network 112, such as to access patient data 120.

Figure 2:
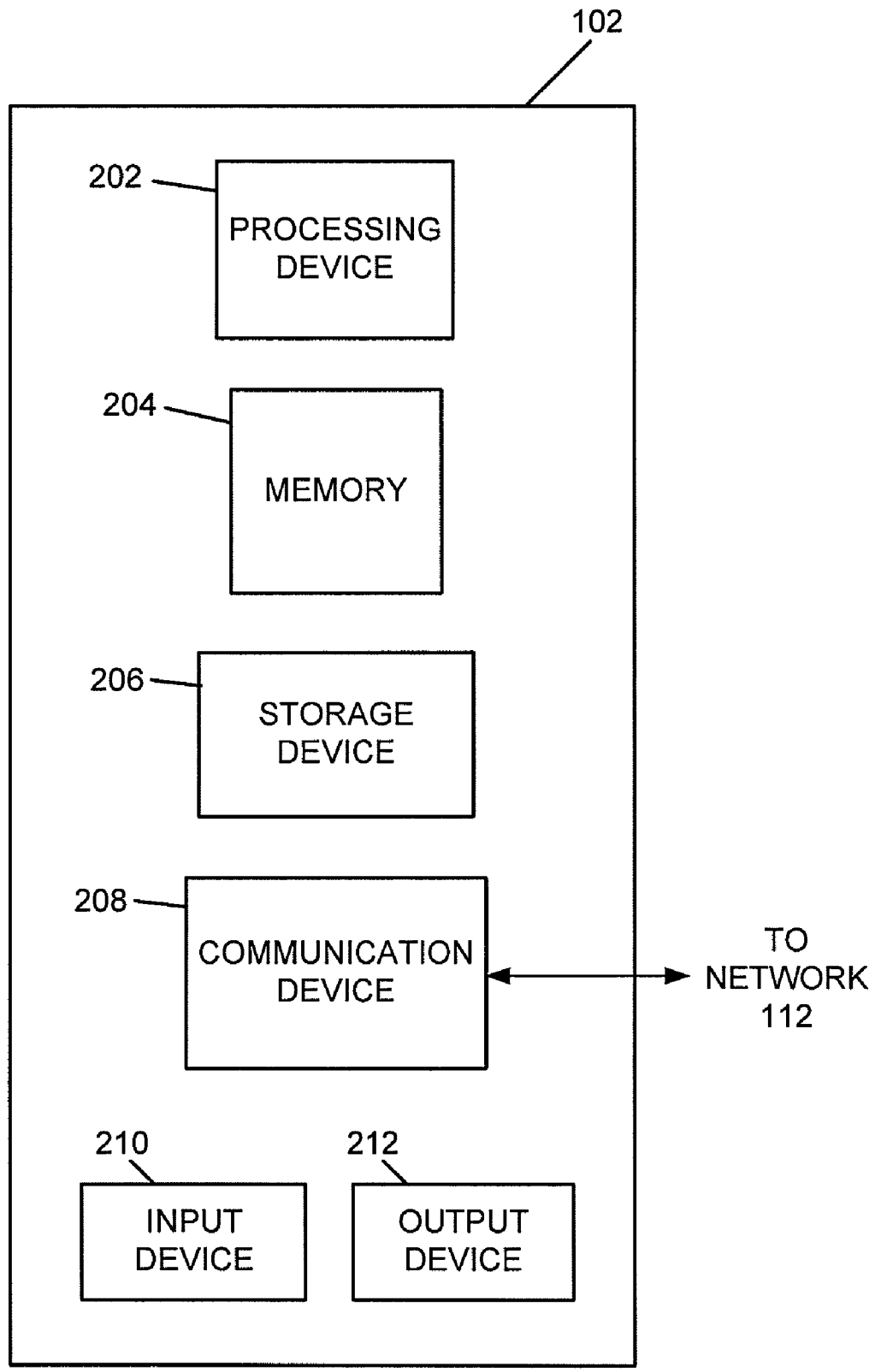
FIG. 2 is a schematic block diagram of an exemplary server of the health care data management system shown in FIG. 1.

FIG. 2 is a schematic block diagram of an exemplary server 102. Server 102 is a computing system that typically includes a processing device 202, memory 204, a storage device 206, a communication device 208, an input device 210, and an output device 212.

In its most basic configuration, server 102 typically includes processing device 202, memory 204, and communication device 208. Other embodiments include other components, such as illustrated in FIG. 2, or yet other components.

Processing device 202 is a device that processes a set of instructions. One example of processing device 202 is a microprocessor. Alternatively, various other processing devices may also be used including central processing units ("CPUs), microcontrollers, programmable logic devices, field programmable gate arrays, digital signal processing ("DSP") devices, and the like. Processing devices may be of any general variety such as reduced instruction set computing (RISC) devices, complex instruction set computing devices ("CISC"), or specially designed processing devices such as an application-specific integrated circuit ("ASIC") device.

Examples of memory 204 include volatile (such as RAM), and non-volatile (such as ROM and flash) memory. In some embodiments, memory 204 is part of processing device 202, while in other embodiments memory 204 is separate from or in addition to that of processing device 202.

In some embodiments, server 102 also includes an additional storage device 206. Storage device 206 stores digital data. For example, some embodiments of server 102 include removable storage or non-removable storage, including, but not limited to, magnetic or optical disks or tape.

Computer storage media includes volatile and nonvolatile, removable and non-removable media implemented in any method or technology for storage of information such as computer readable instructions, data structures, program modules or other data. Memory 204 and storage device 206 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by server 102. Any such computer storage media may be part of server 102.

In some embodiments, memory 204 and/or storage device 206 store data instructions including one or more of an operating system, application programs, other program modules, and program data.

Server 102 also includes communication device 208 that allows server 102 to communicate with other devices, such as across network 112 (shown in FIG. 1). Communications device 208 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. Examples of communication media include wired media such as a wired network or direct-wired connection, and wireless media such as acoustic, radio frequency, infrared and other wireless media. The term computer readable media as used herein includes both storage media and communication media.

In some embodiments, server 102 includes one or more input devices 210, such as a keyboard, mouse, pen, voice input device, touch input device, or other input device. Some embodiments include one or more output devices 212, such as a display, speaker, printer, or other output device.

The computing system described above with reference to server 102 is also an example of other computing systems described herein. For example, in some embodiments records administrator computing system 104, emergency vehicle computing system 106, hospital computing system 108, and patient computing system 110 are also computing systems as described above.

Figure 3:
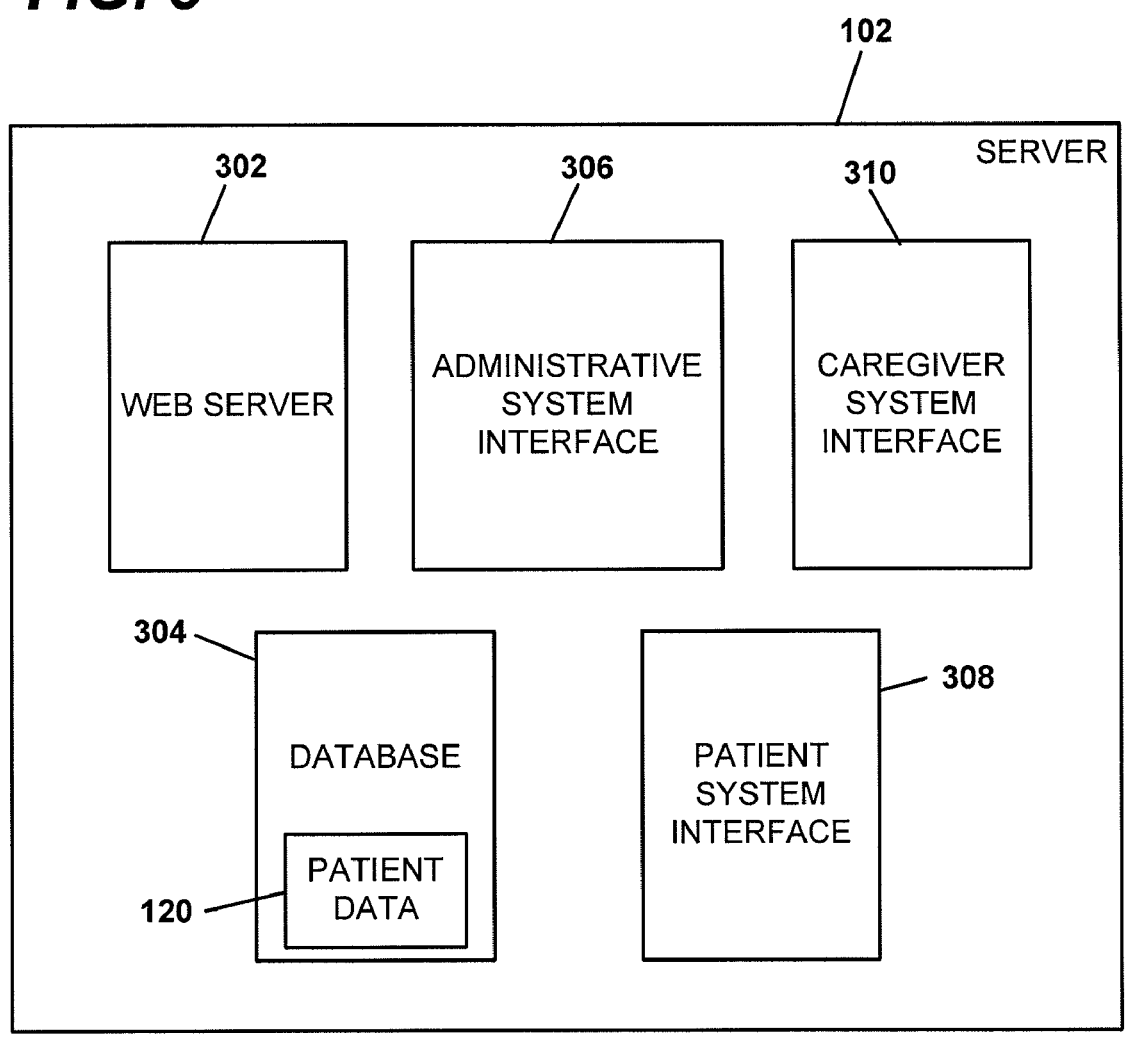
FIG. 3 is a functional block diagram of the server shown in FIG. 2.

FIG. 3 is a functional block diagram of an exemplary server 102. Server 102 includes Web server 302, database 304, administrative system interface 306, patient system interface 308, and caregiver system interface 310. Other embodiments include more or fewer features, functions, or modules.

Web server 302 is a computer program that operates to communicate data defining one or more Web pages, such as across network 112 (shown in FIG. 1). Examples of Web server software applications include Internet Information Services from Microsoft Corporation and Apache HTTP Server. In some embodiments Web server operates to receive Hyper Text Transfer Protocol (HTTP) requests from clients (such as systems 104, 106, 108, or 110) and to serve HTTP responses along with data content, such as Web pages formatted in Hypertext Markup Language (HTML).

Database 304 stores patient data 120. Patient data 120 is typically associated with a single patient, such that database 304 includes a plurality of patient data records.

In some embodiments server 102 includes separate interface modules for communicating with particular groups of users. For example, server 102 includes administrative system interface 306 for communicating with an administrator (such as through records administrator system 104), patient system interface 308 for communicating with a patient (such as through patient computing system 110), and caregiver system interface 310 for communicating with a caregiver (such as through emergency vehicle system 106 or hospital system 108). It is sometimes desirable to provide separate interfaces for different groups of users, such as to provide different access rights to each group. For example, a patient using patient computing system 110 is typically limited to accessing his or her own patient data 120, while a caregiver using a caregiver computing system such as system 108 will typically have access to the patient data of more than one patient. In some embodiments system interfaces 306, 308, and 310 are custom software applications that control access rights and define particular Web pages to be displayed to the associated group. In some embodiments, system interfaces 306, 308, and 310 also define one or more communication protocols and operate to communicate data according to the protocols. For example, in some embodiments some or all communication between server 102 and one or more groups of users occurs through one of system interfaces 306, 308, and 310 rather than through Web server 302. In this way, data is communicated between the user system (e.g., emergency vehicle system 106) and server 102 according to a customized or other communication protocol.

Figure 4:
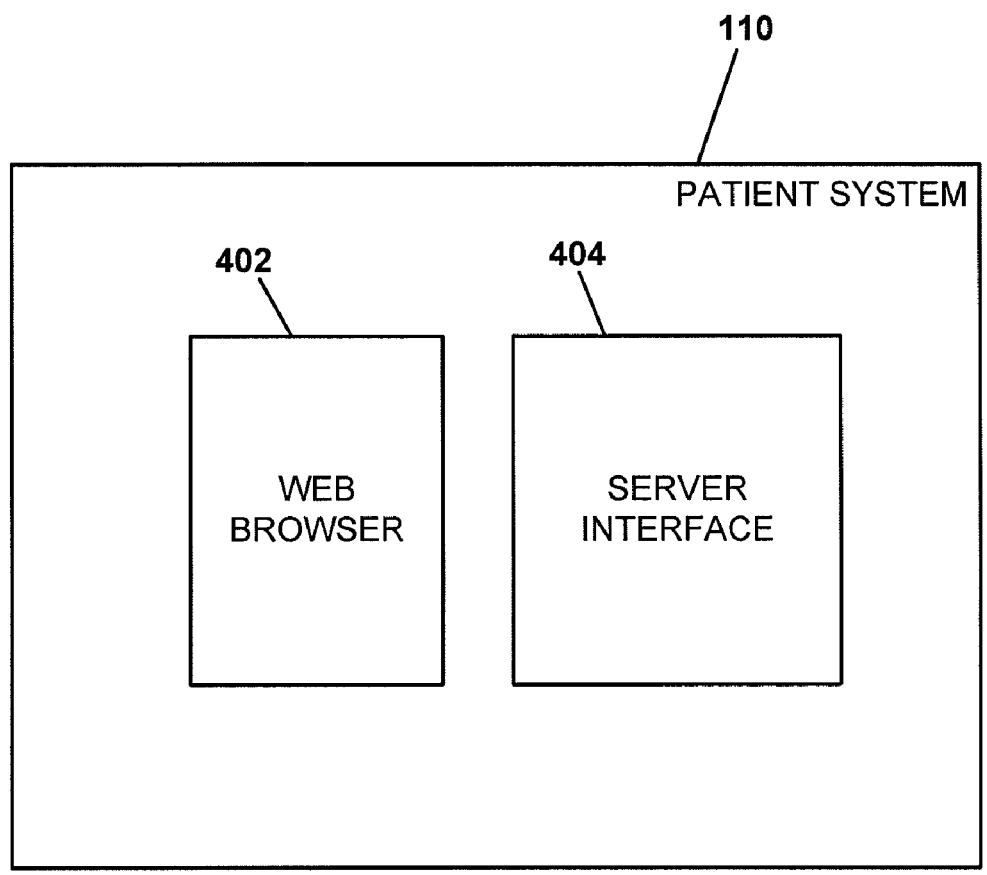
FIG. 4 is a functional block diagram of an exemplary patient system of the health care data management system shown in FIG. 1.

FIG. 4 is a functional block diagram of an exemplary patient computing system 110. Patient computing system 110 includes Web browser 402 and server interface 404.

Web browser 402 is a software application operating on patient computing system 110 that operates to communicate with Web server 302 (shown in FIG. 3), such as to display Web pages from Web server 302. In some embodiments Web browser operates to send HTTP requests to Web server 302 and to receive HTTP responses along with data content from Web server 302. Examples of Web browser 402 include INTERNET EXPLORER® internet browser by Microsoft Corporation and the FIREFOX® Internet browser by the Mozilla Foundation.

In some embodiments patient computing system 110 includes server interface 404 for communicating with patient system interface 308 (shown in FIG. 3) of server 102. In some embodiments, server interface 404 is a custom software application that defines one or more communication protocols and operates to communicate data according to the protocols.

The system described above with reference to patient computing system 110 is also an example of other systems described herein, such as records administrator system 104, emergency vehicle system 106, and hospital system 108. In some embodiments these systems include additional modules. For example, in some embodiments hospital system 108 includes a hospital database interface for accessing data available through a hospital intranet or database.

Figure 5:
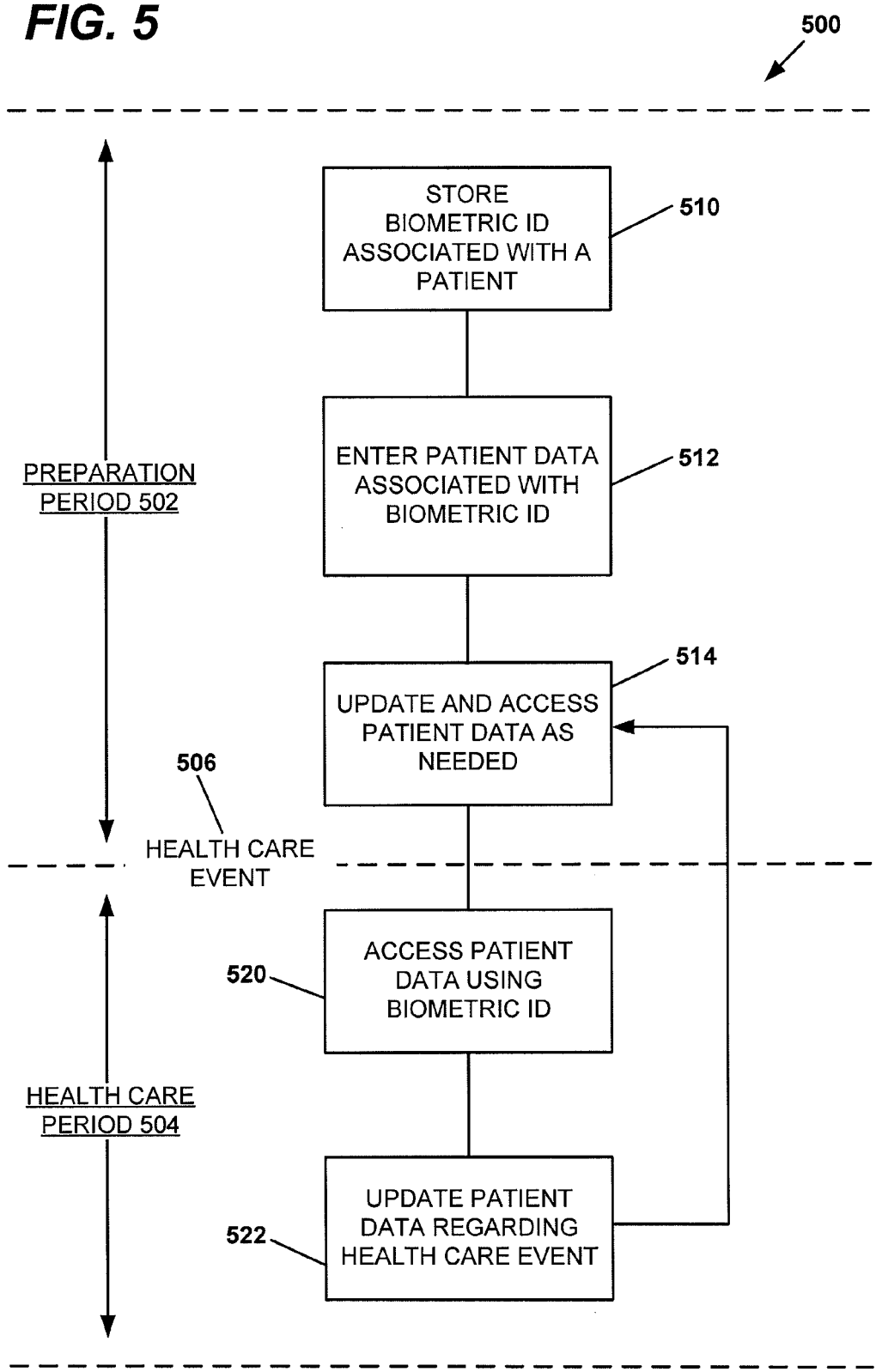
FIG. 5 is a flow chart illustrating an exemplary method of operating a health care data management system according to the present disclosure.

FIG. 5 is a flow chart illustrating an exemplary method 500 of operating a health care data management system. Method 500 includes two periods—a preparation period 502 and a health care period 504, which are separated by a health care event 506. Preparation period 502 includes operations 510, 512, and 514. Health care period includes operations 520 and 522.

Preparation period 502 begins with operation 510 to store a biometric identifier associated with a patient. In some embodiments operation 510 is a user registration process. For example, a fingerprint is scanned and a biometric identifier is generated based on unique features of the fingerprint. The biometric identifier is then stored in memory, such as on a server.

Operation 512 is then performed to enter patient information associated with the biometric identifier. For example, the patient's name and date of birth are stored in a database record associated with the biometric identifier. In some embodiments, patient data 120 (shown in FIG. 1) is stored in the database and associated with the biometric identifier. In some embodiments operation 512 is performed before operation 510.

After operations 510 and 512, operation 514 is performed to update and access patient information as needed. For example, a patient accesses the patient info on server 102 through patient computing system 110 (shown in FIG. 1). The patient is allowed to edit and update some or all of the patient information as needed. The patient also adds additional patient information in some embodiments.

Health care event 506 separates preparation period 502 from health care period 504. Health care event 506 is, for example, an event which causes a caregiver to access patient data. Examples of health care events include a health emergency (e.g., heart attack), a routine health checkup, a visit to a physician's office, the performance of a diagnostic test, prescribing a medication, performing an immunization, death, and birth of a child.

Upon the occurrence of health care event 506, operation 520 is performed by a caregiver to access patient data using the biometric identifier. In some embodiments, operation 520 involves reading a biometric identifier from a patient, such as a fingerprint. The biometric identifier is matched with patient data associated with the biometric identifier. The caregiver is then given access to the patient data associated with the patient. The patient data assists the caregiver in providing proper health care to the patient.

In some embodiments, health care costs are reduced because caregivers are able to provide proper health care and do not perform unnecessary testing or treatment. For example, if a test has already been performed, information about the results of the test are available to the caregiver such that retesting may not be necessary. Similarly, if a therapy has already been provided (or tests have already confirmed that therapy is not necessary), the caregiver is provided with this information so that the caregiver does not unnecessarily provide the therapy. For example, if a patient has already been immunized against a condition, the caregiver is provided with that information to prevent the caregiver from re-immunizing the patient. Health care costs are reduced in some embodiments by preventing improper treatment. For example, if a patient is allergic to a particular drug, allergy information is provided to the caregiver so that the caregiver does not administer that drug.

In some embodiments, using the biometric identifier provides fast and secure access to patient information that is authenticated as being associated with the patient by using the biometric identifier. As a result, a caregiver is able to quickly access the patient information needed to provide proper health care. As a result, treatment is not delayed while caregivers wait to obtain health records, such as by fax from the patients primary caregiver.

Operation 522 is then performed to update patient data regarding the health care event. For example, a caregiver enters information about the health care event (such as a description of a medical condition or diagnostic test that was performed), how the event was treated (such as by prescribing a medication), and the results of the event (such as that the medication took away the symptoms). Any other patient information may be updated as desired during operation 522.

In some embodiments, operation 522 involves billing of medical expenses incurred. In some embodiments, caregivers provide invoices (such as by sending the invoices to server 102, shown in FIG. 1). In some embodiments, invoices are then electronically delivered to the patient (such as through patient system 110, shown in FIG. 1). In other embodiments, invoices are sent electronically to a health care company or governmental health care system. Examples of governmental health care systems include Medicare and Medicaid. In some embodiments billing is performed more quickly. In some embodiments, records of invoices and associated payments (by patient or health care company/system) are stored with the patient's records.

In some embodiments operation 522 also involves medical transcription. For example, a caregiver records dictation of medical care or diagnosis that was performed, such as in a digital audio file. The digital audio file is then transferred to server (e.g., server 102, shown in FIG. 1). In some embodiments, the server transfers the file to a medical transcription service that converts the dictation into a medical record. The medical record is then transferred back to the server and stored in the patient's records. In some embodiments the audio file is also or alternatively stored in the patient's records.

Health care period 504 is then concluded, such that method 500 returns to operation 514 of preparation period 502, where patient data is updated or accessed as needed.

Example embodiments will now be described with reference to exemplary graphical user interfaces. In some embodiments the graphical user interfaces are defined by Web pages that are hosted on a server 102 of system 100. Users can access these pages using a Web browser.

Figure 6:
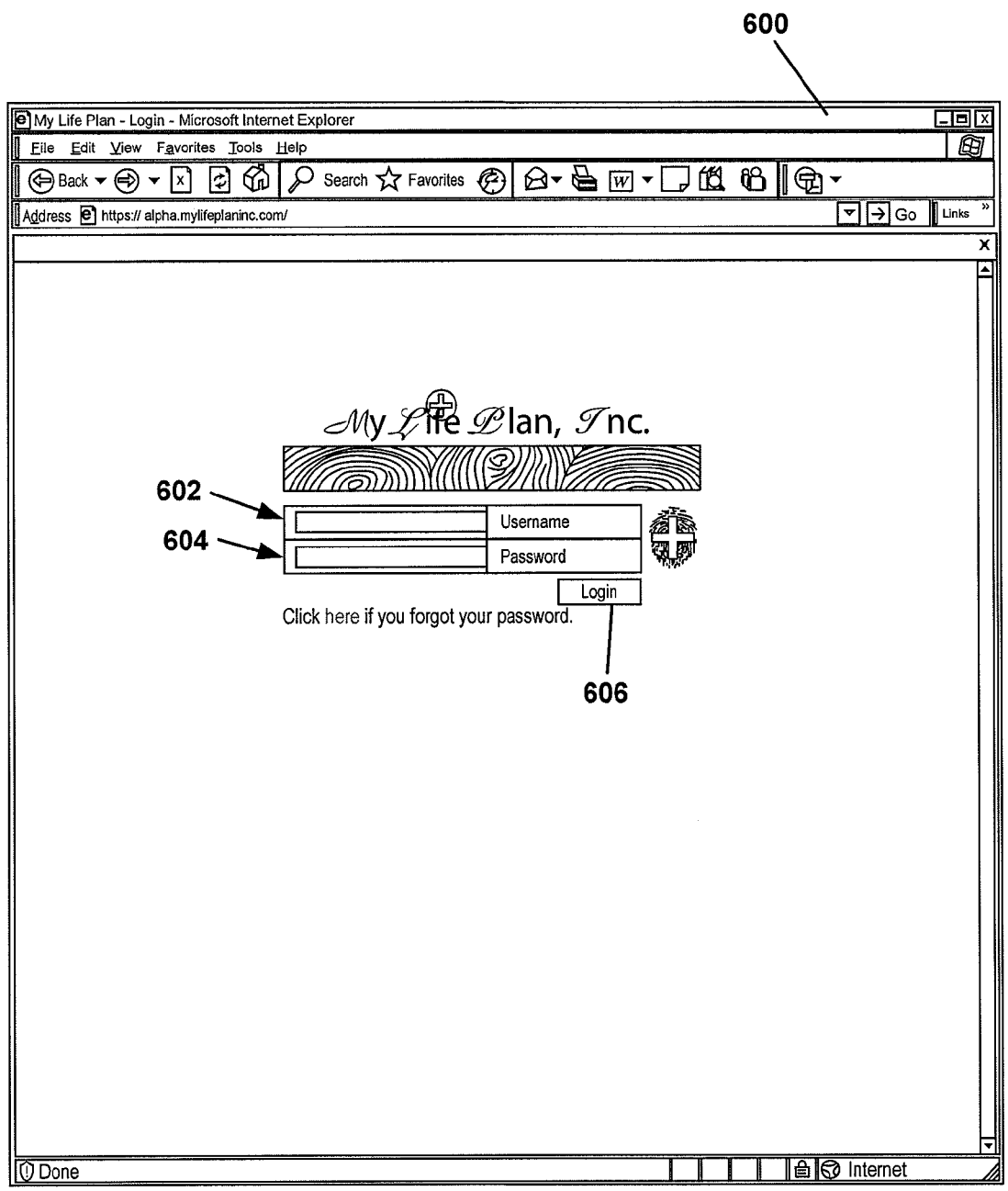
FIG. 6 is a screen shot of an exemplary login interface according to the present disclosure.

FIG. 6 is a screen shot of an exemplary login interface 600. Login interface 600 includes username prompt 602, password prompt 604, and login button 606.

In some embodiments a graphical user interface begins with login interface 600. In some embodiments, login interface is defined by server 102 and is displayed by a computing system, such as patient computing system 110 (or another computing system including records administrator system 104, emergency vehicle system 106, or hospital system 108), shown in FIG. 1.

Login interface 600 prompts a user to enter a username and a password in order to proceed. Username prompt 602 prompts the user for a username and password prompt 604 prompts the user for a password.

After the username and password have been entered by a user, the user then selects login button 606. In some embodiments, upon selection of login button 606 the username and password are communicated to a server for evaluation. If the username and password match a username and password for an active user account, the user is allowed to gain access into the system. For example, a home interface is next displayed in some embodiments, such as shown in FIG. 7.

In some embodiments a user account is associated with a role. Examples of user roles include a patient role, an administrator role, and a caregiver role. The role associated with a user account defines the access rights and permissions available to that set of users. In some embodiments different user interface displays are displayed to different users according to the associated user role.

Figure 7:
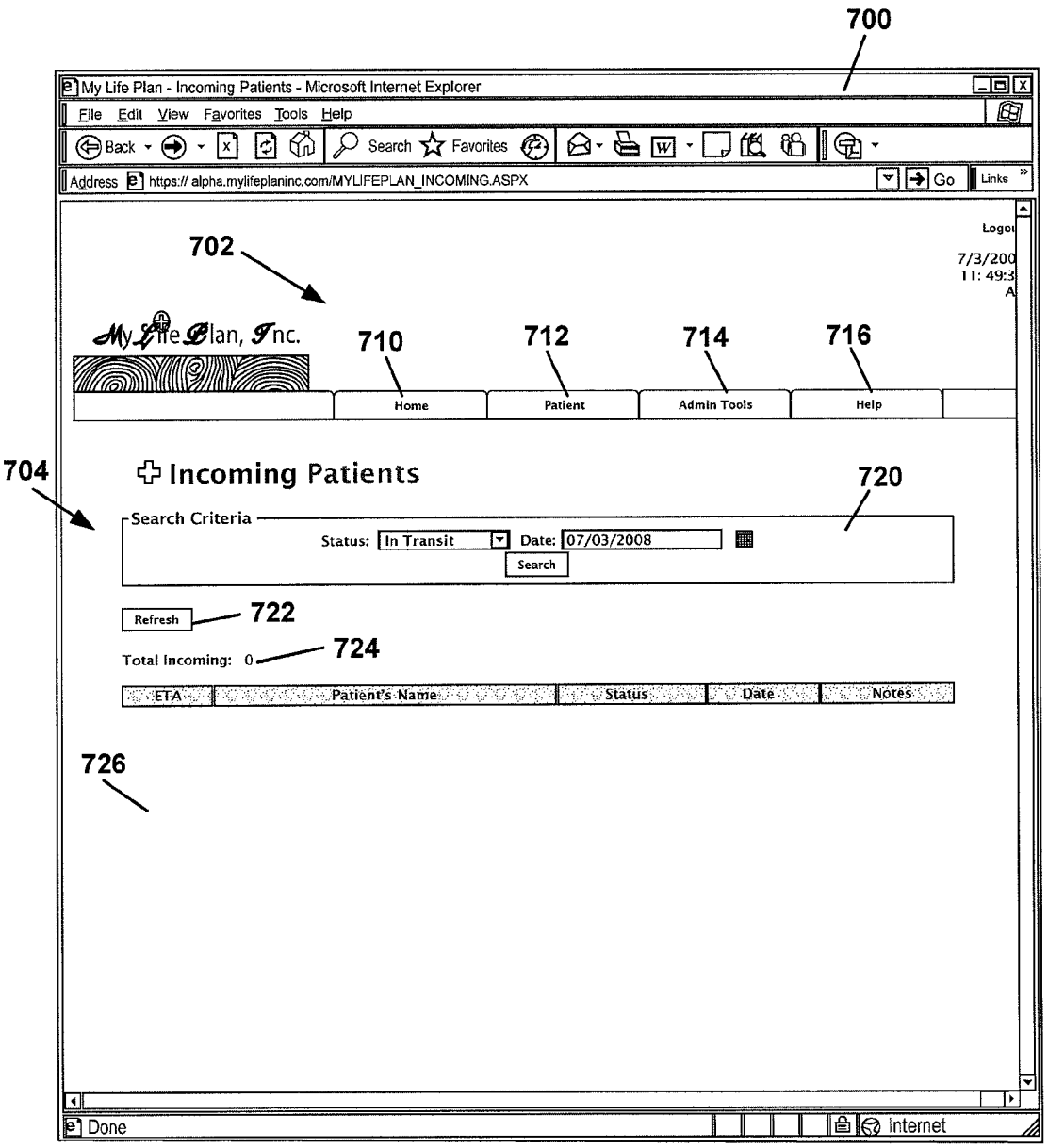
FIG. 7 is a screen shot of an exemplary home interface according to the present disclosure.

FIG. 7 is a screen shot of an exemplary home interface 700. Home interface 700 includes navigation tabs 702 and incoming patients display 704. Navigation tabs 702 include home tab 710, patient tab 712, administrative tools tab 714, and help tab 716. Incoming patients display 704 includes search window 720, refresh button 722, total incoming display 724, and search result window 726. Search window 720 includes status prompt 730, date prompt 732, and search button 734.

Navigation tabs 702 are displayed on many interface pages to allow the user to quickly navigate among various pages of the graphical user interface. In some embodiments, tabs 702 include home tab 710, patient tab 712, administrative tools tab 713, and help tab 716. In some embodiments, navigation tabs 702 provide a drop-down menu identifying a set of available web pages when one of the navigation tabs 702 is selected. Selection of a navigation tab includes a mouse-over or click of an input device on one of the navigation tabs 702, in some embodiments. A keyboard input or other input signal is provided to select a navigation tab 702 in other embodiments.

Home tab 710 is a navigation tab that causes home interface 700 to be displayed.

Figure 12:
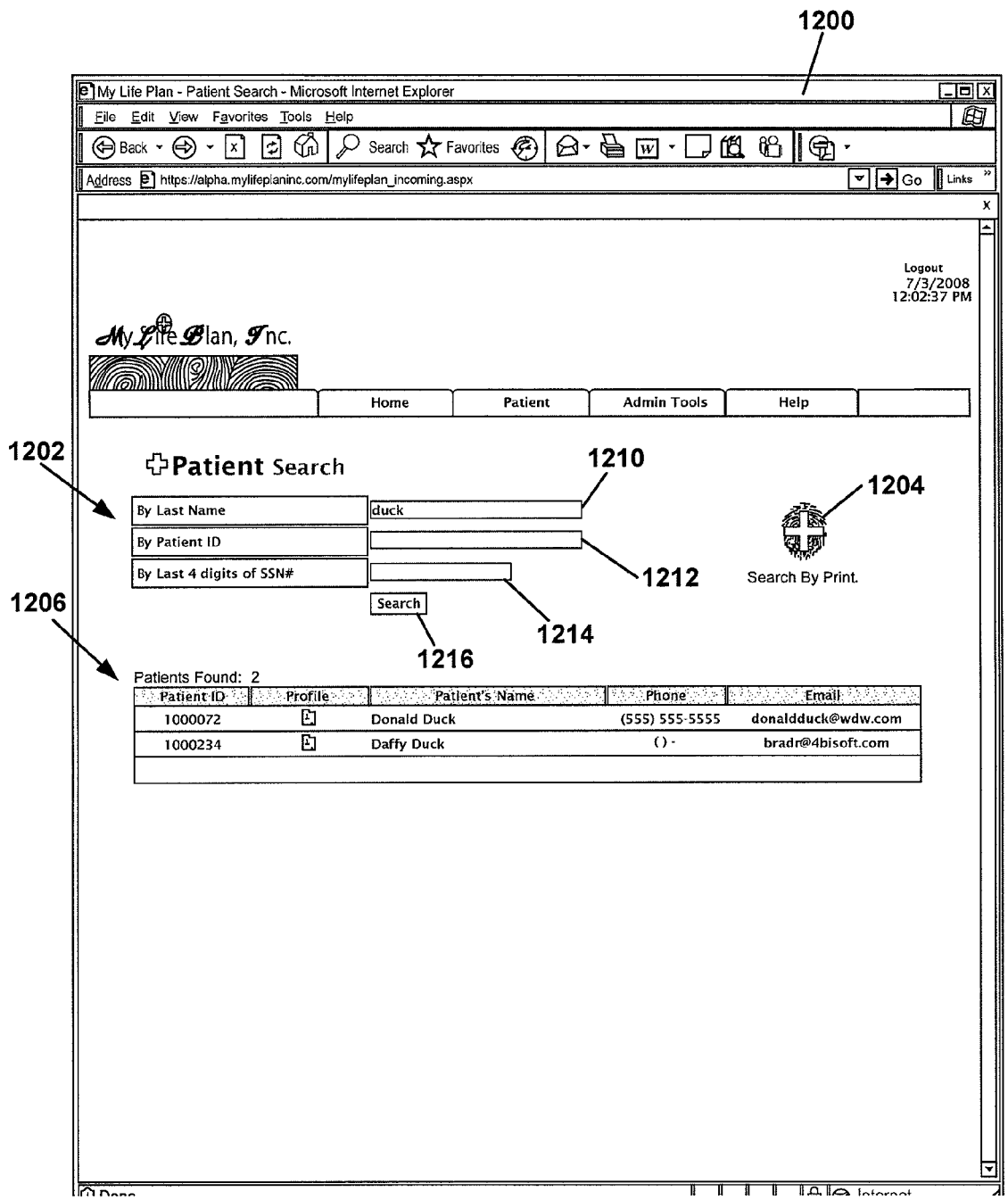
FIG. 12 is a screen shot of an exemplary patient search interface according to the present disclosure.
Figure 13:
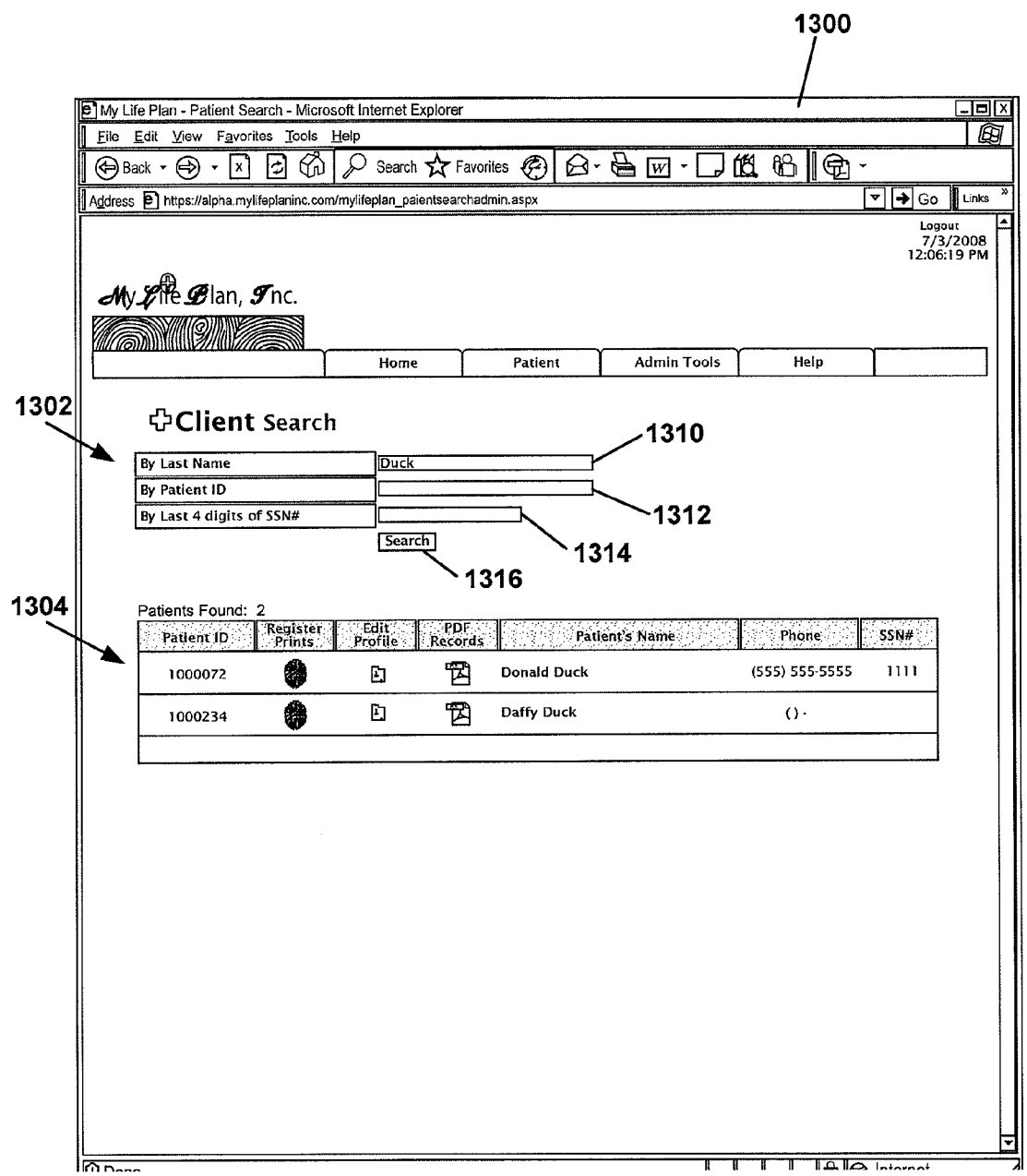
FIG. 13 is a screen shot of an exemplary client search interface according to the present disclosure.

Patient tab 712 provides a drop down list of options. Exemplary options include Patient Search and Patient Search Admin. If the user selects Patient Search, the Patient Search interface is displayed, such as shown in FIG. 12. If the user selects Patient Search Admin, the Client Search interface is displayed, such as shown in FIG. 13.

Figure 14:
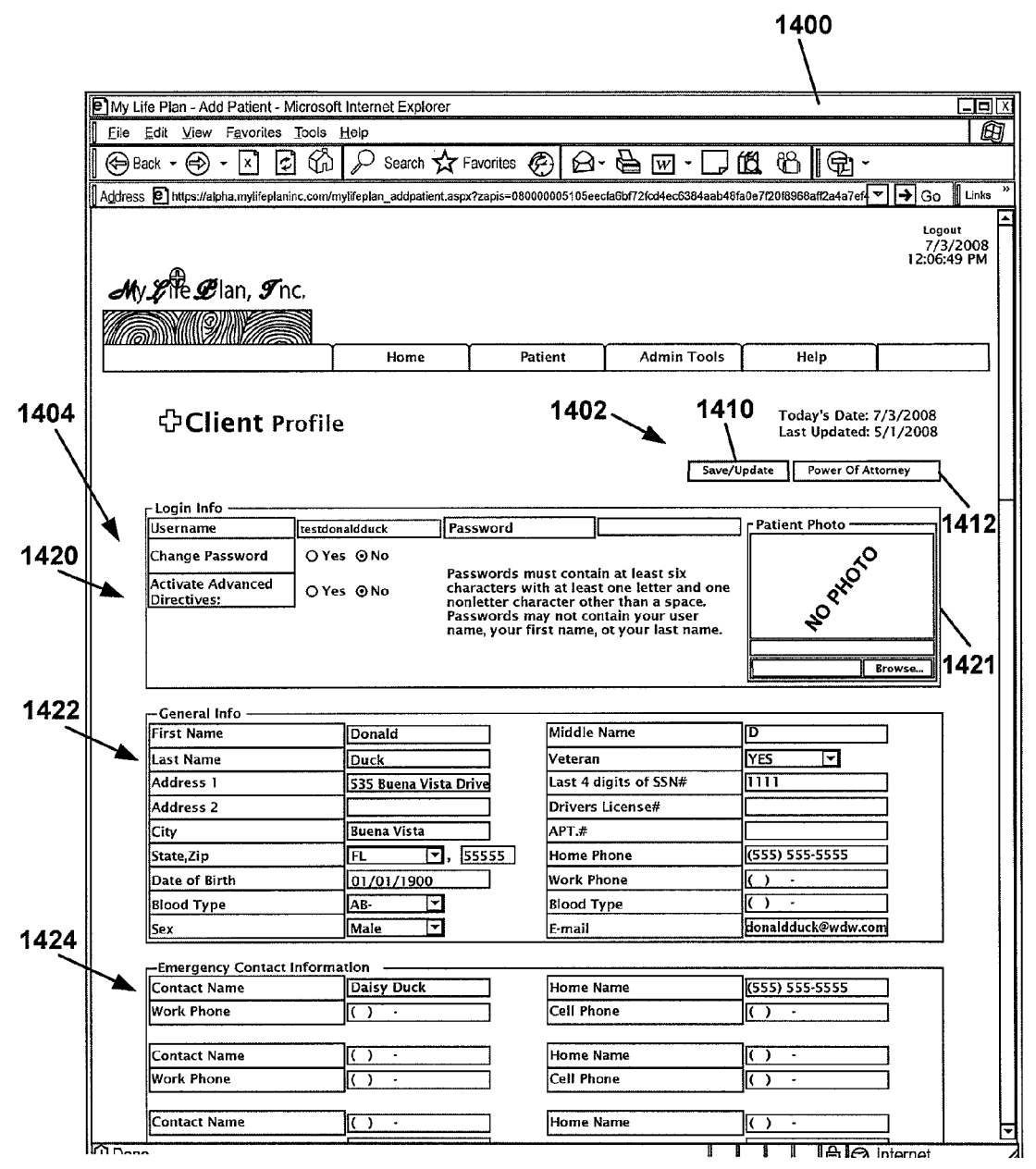
Figure 16:
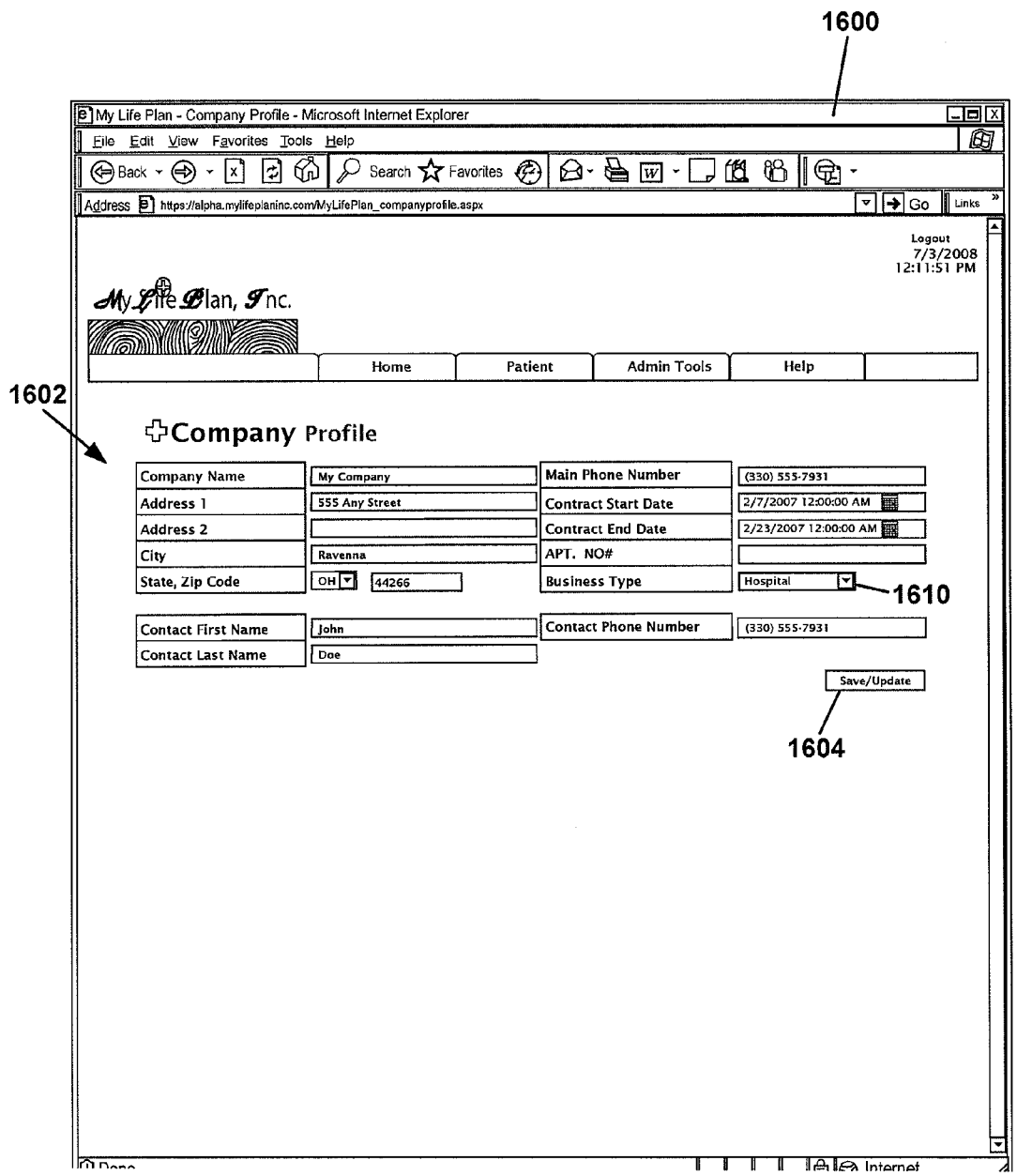
FIG. 16 is a screen shot of an exemplary company profile interface according to the present disclosure.
Figure 17:
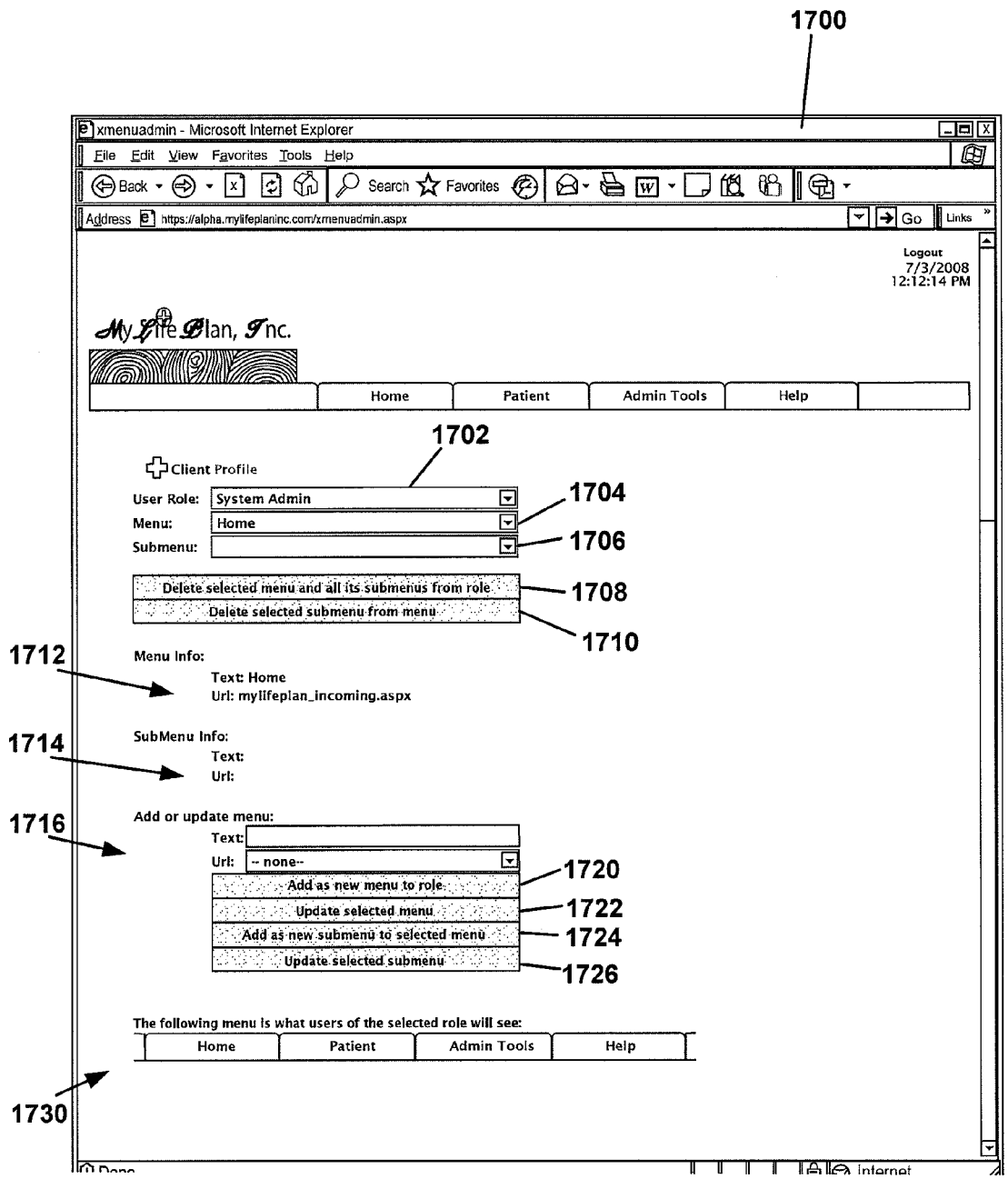
FIG. 17 is screen shot of an exemplary menu manager interface according to the present disclosure.
Figure 18:
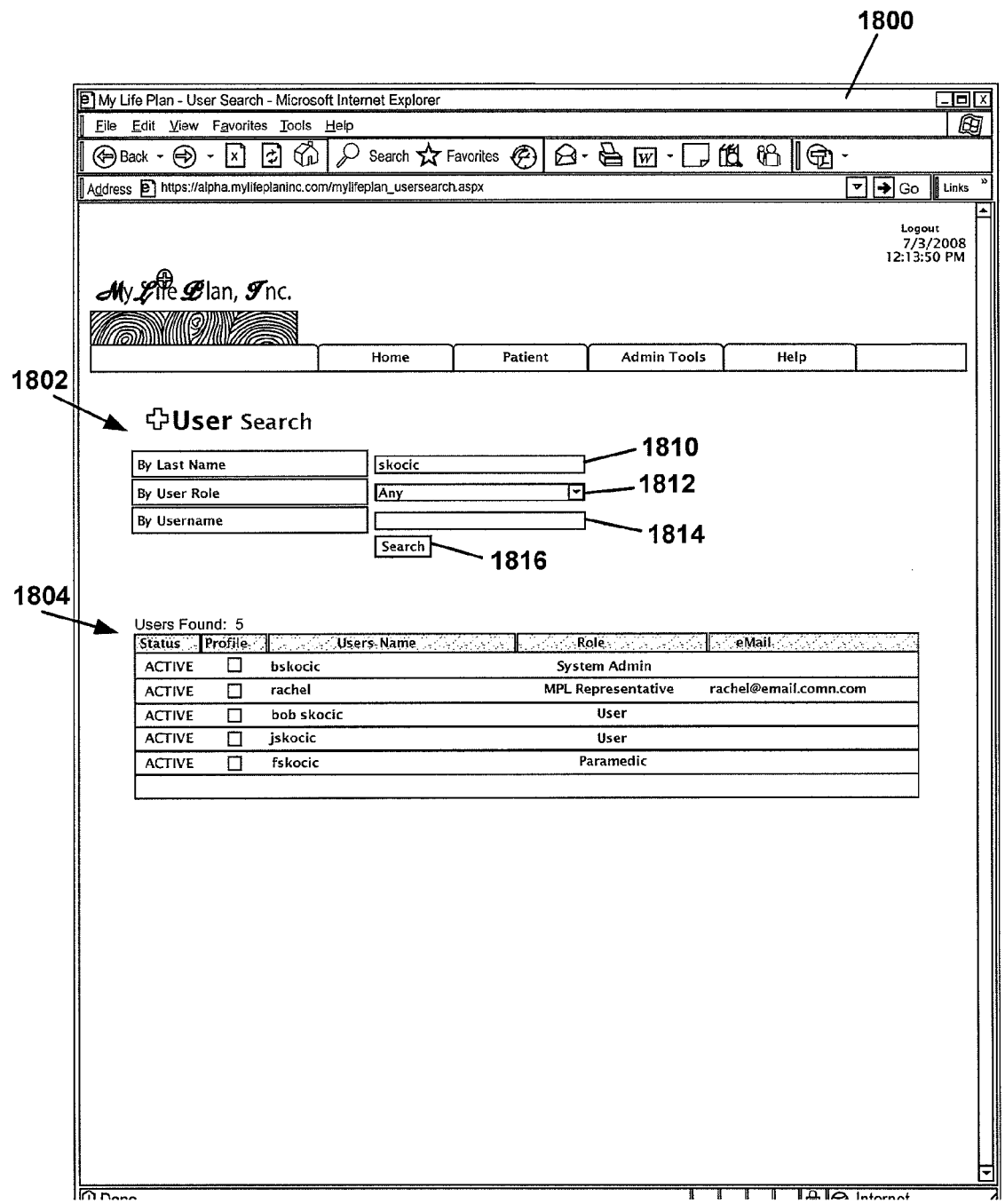
FIG. 18 is a screen shot of an exemplary user search interface according to the present disclosure.
Figure 19:
FIG. 19 is a screen shot of an exemplary user profile interface according to the present disclosure.
Figure 20:
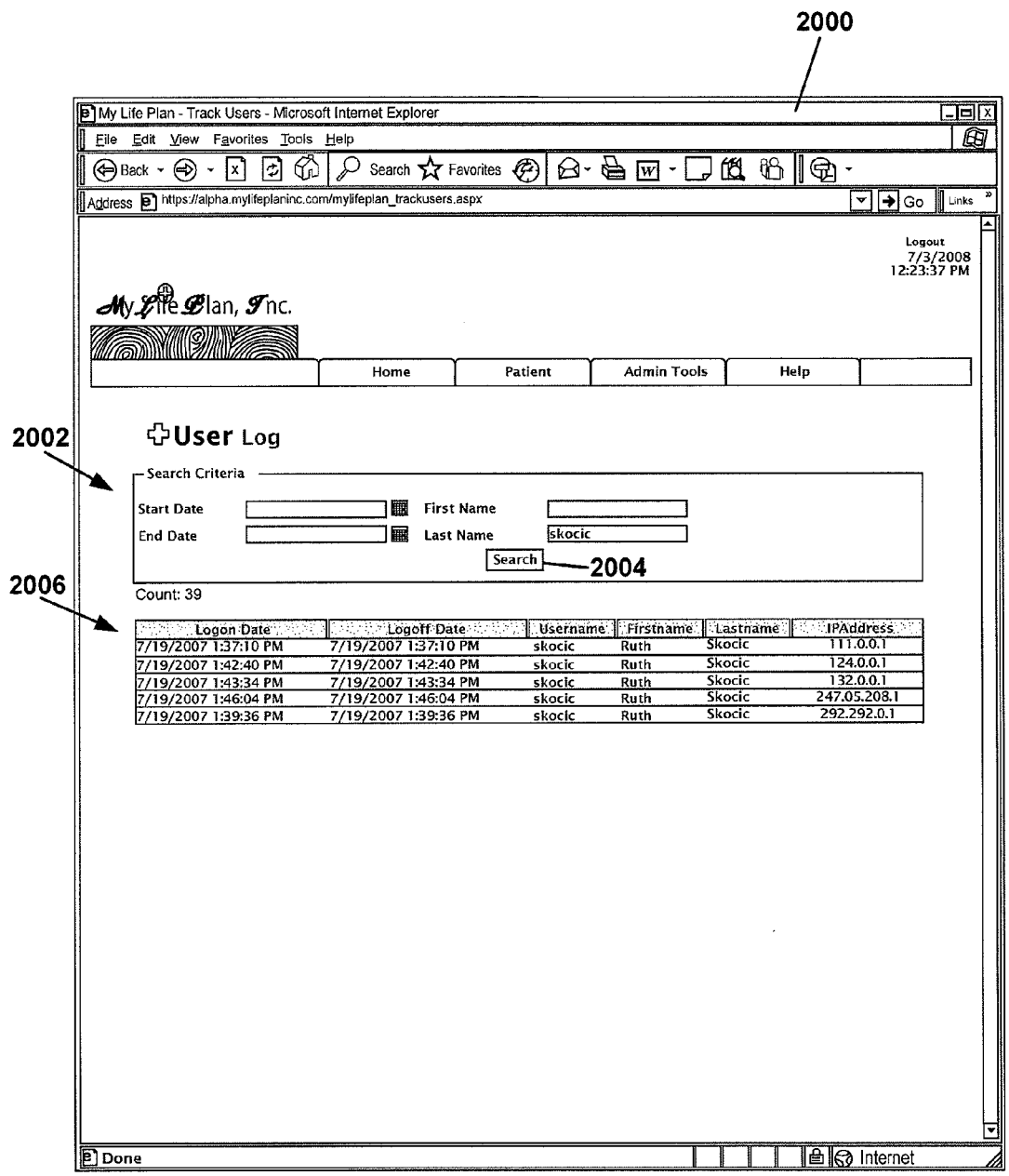
FIG. 20 is a screen shot of an exemplary user log interface according to the present disclosure.
Figure 21:
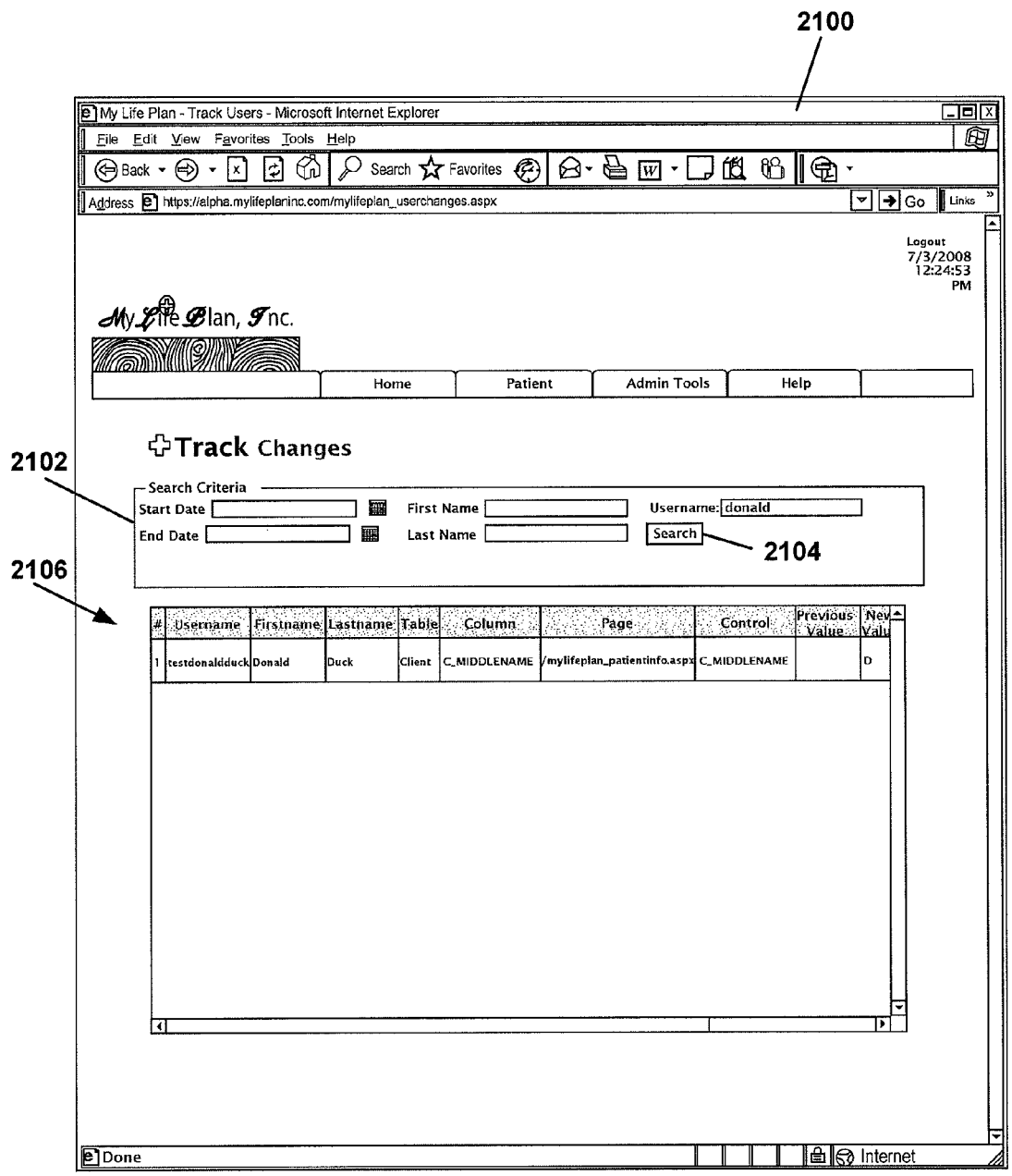
FIG. 21 is a screen shot of an exemplary track changes interface according to the present disclosure.
Figure 22:
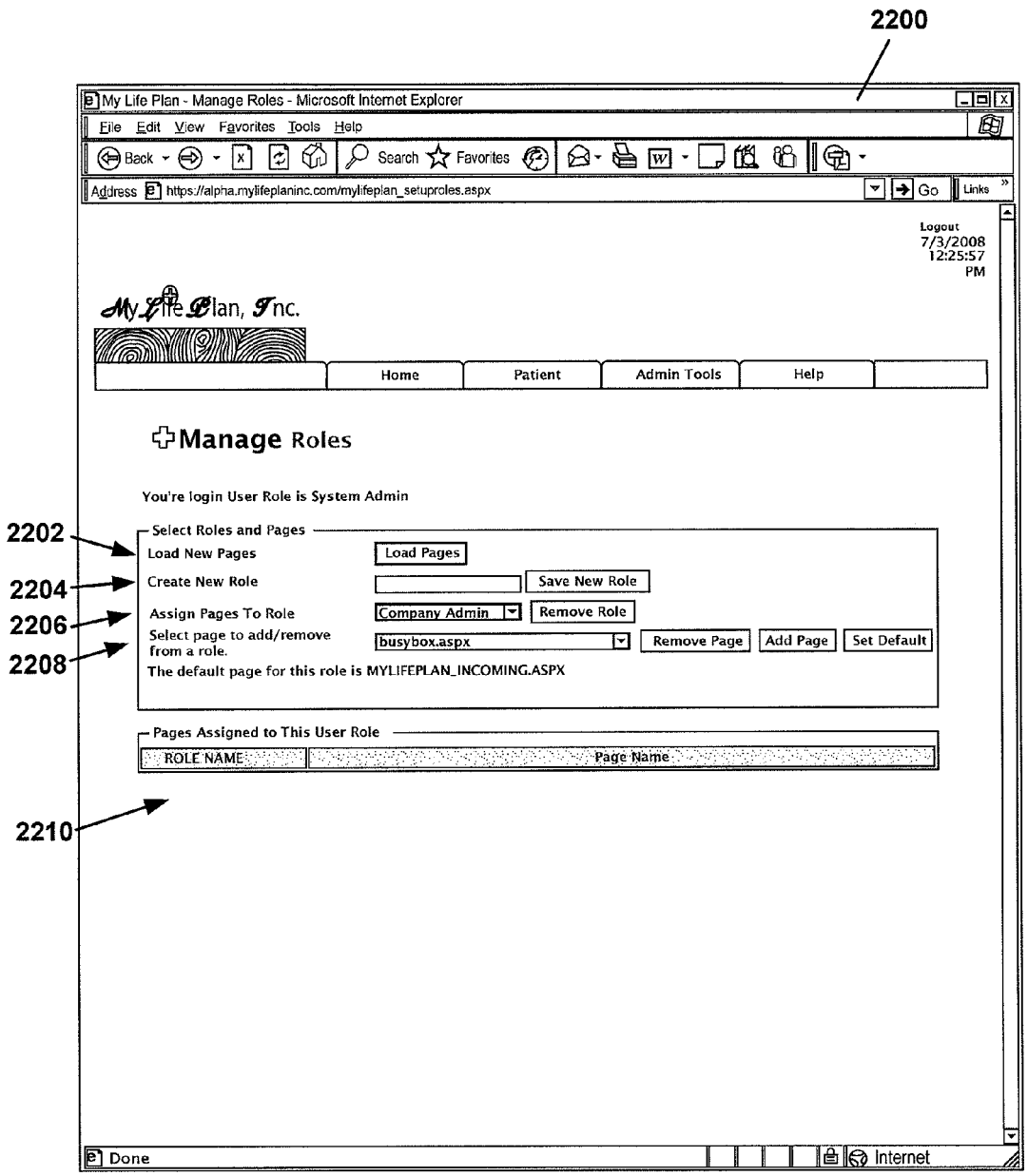
FIG. 22 is a screen shot of an exemplary manage roles interface according to the present disclosure.

Administrative tools tab 714 provides a drop down list of options. Exemplary options include Company Profile, Menu Manager, User Search, Add Patient, User Profile, Track Users, Track Changes, and Manage Roles. If the user selects Company Profile, the Company Profile interface is displayed, such as shown in FIG. 16. If the user selects Menu Manager, the Menu Manager interface is displayed, such as shown in FIG. 17. If the user selects User Search, the User Search interface is displayed, such as shown in FIG. 18. If the user selects Add Patient, a blank client profile interface is displayed, such as shown in FIG. 14. If the user selects User Profile, the User Profile interface is displayed, such as shown in FIG. 19. If the user selects Track Users, the User Log interface is displayed, such as shown in FIG. 20. If the user selects Track Changes, the Track Changes interface is displayed, such as shown in FIG. 21. If the user selects Manage Roles, the Manage Roles interface is displayed, such as shown in FIG. 22.

Figure 23:
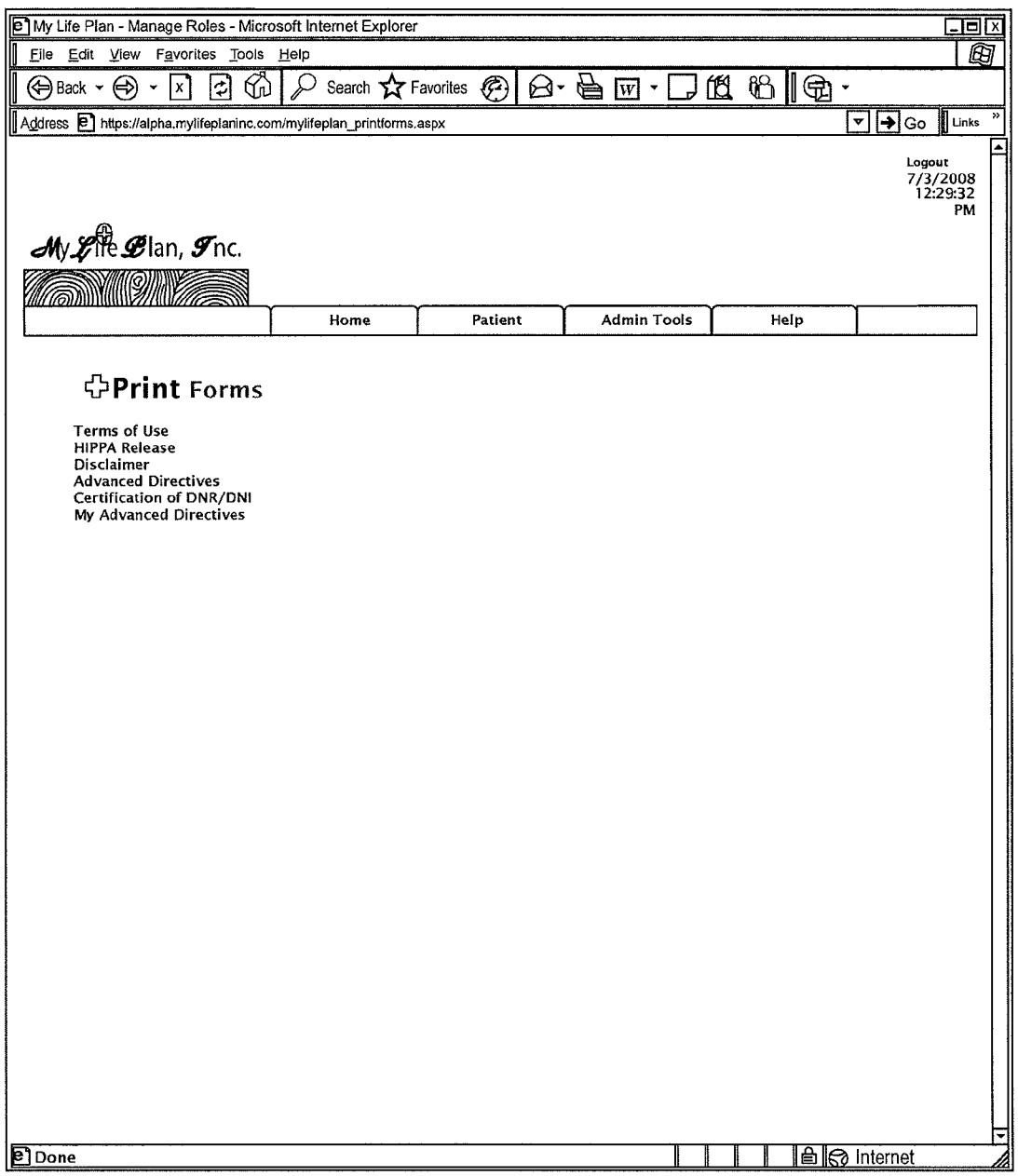
FIG. 23 is a screen shot of an exemplary print forms interface according to the present disclosure.

Help tab 716 provides a drop down list of options. Exemplary options include Print Forms, About, and Contact Us. If the user selects Print Forms, the Print Forms interface is displayed, such as shown in FIG. 23. If the user selects About, the About interface is displayed. The About interface provides information about the people or company that are currently operating the system. Information includes a history of the company, biographies of individuals associated with the system, an identification of a version number of the system, a description of the mission or purpose of the company, information about the contract that the user has with the company, or any other desired information. If the user selects Contact Us, the Contact Us interface is displayed which provides contact information to the user. Examples of contact information include an address, telephone number, e-mail address, and an online form for submission of an e-mail message.

Incoming patients display 704 includes search window 720, refresh button 722, total incoming display 724, and search results window 726. The incoming patients display 704 is displayed on home interface 700 to allow a caregiver to quickly locate information regarding patients.

Search window 720 includes status prompt 730, date prompt 732, and search button 734. In some embodiments, when status prompt 730 is selected by a user, a drop down window is displayed that provides a list of available status identifiers. Examples of status identifiers include All, Arrived, Cancelled, In Transit, and Patient Expired. The All status identifier allows a user to search for all patients regardless of status, and includes patients associated with all of the other status identifiers. The Arrived status identifier is associated with patients that have arrived at the health care facility. The Cancelled status identifier is associated with a patient that was previously indicated with another status identifier (such as In Transit or Arrived), but was subsequently cancelled, such as due to the recovery of the patient to a sufficient level that further health care is not required. The In Transit status identifier is associated with a patient that is in transit to the health care facility. In transit includes a patient that is being transported by an emergency vehicle or a patient who is expected, such as because a telephone call was received indicating that the patient is coming to the health care facility. The Patient Expired status identifier is associated with a patient that has died.

Date prompt 732 allows a user to identify a date to be searched. In some embodiments when a user selects the date prompt 732 a calendar is displayed. The user then navigates to the appropriate date and selects that date or range of dates.

After the status and date have been selected, a user then selects search button 734 to submit the status and date information. A search is then conducted to identify all users having the selected status identifier on the selected date. The search results are then displayed in search results window 726.

In some embodiments, the search is performed as follows. The search criteria are received by a server computing system indicating the status identifier and the date to be searched. Patient information, such as stored in a database of the server is then searched to find patients that match the search criteria. The resulting list of patients is then returned to the user's computing system that requested the search results and is displayed in search results window 726, such as shown in FIG. 8.

Figure 8:
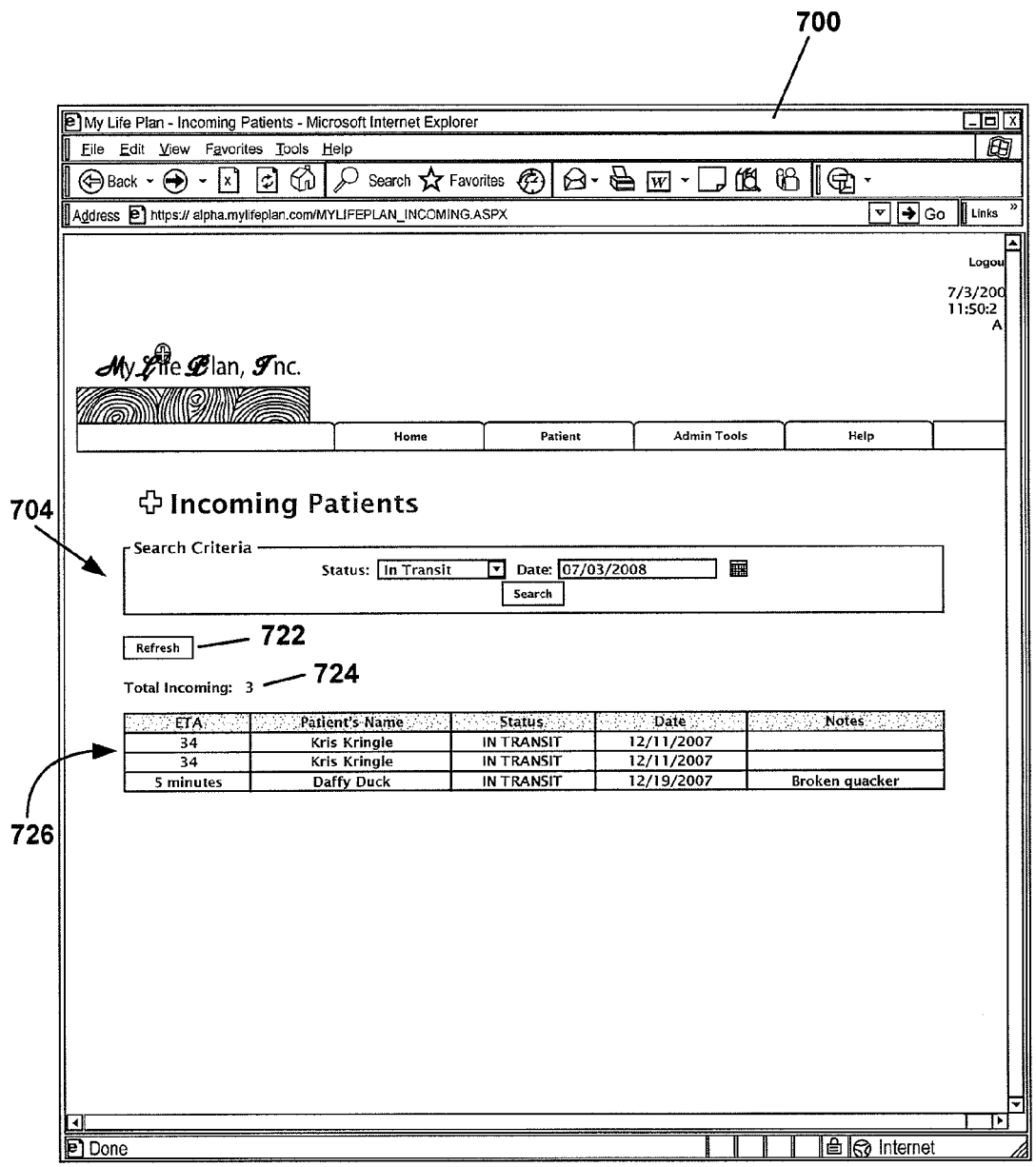
FIG. 8 is a screen shot of the home interface shown in FIG. 7 after running a search.

FIG. 8 is a screen shot of an exemplary home interface 700 after running a search. As described above, home interface 700 includes incoming patients display 704. Incoming patients display 704 includes search window 720, refresh button 722, total incoming display 724, and search result window 726. Search window 720 includes status prompt 730, date prompt 732, and search button 734.

The example illustrated in FIG. 8 shows home interface 700 after an exemplary search has been conducted for patients matching particular search criteria. The search criteria in this example included patients having a status identifier of In Transit on the date of Jul. 3, 2008.

Search results window 726 displays three search results that were found for the exemplary search. For each search result, information is displayed. In this example, the information includes an Estimate Time of Arrival (ETA), Patient's Name, Status, Date, and Notes. Other search results have other information displayed as appropriate for the particular search. For each search result, the Patient's Name is a hyperlink to the associated Patient Profile interface. For example, the user selects the patient's name "Kris Kringle" associated with the first search result to bring up Patient Profile Interface 900, shown in FIG. 9.

If a user desires to update the search results display without changing the search criteria, refresh button 722 is selected. Upon selection of refresh button 722, a new search is performed using the previously defined search criteria. The results are displayed in search results window 726.

Figure 9:
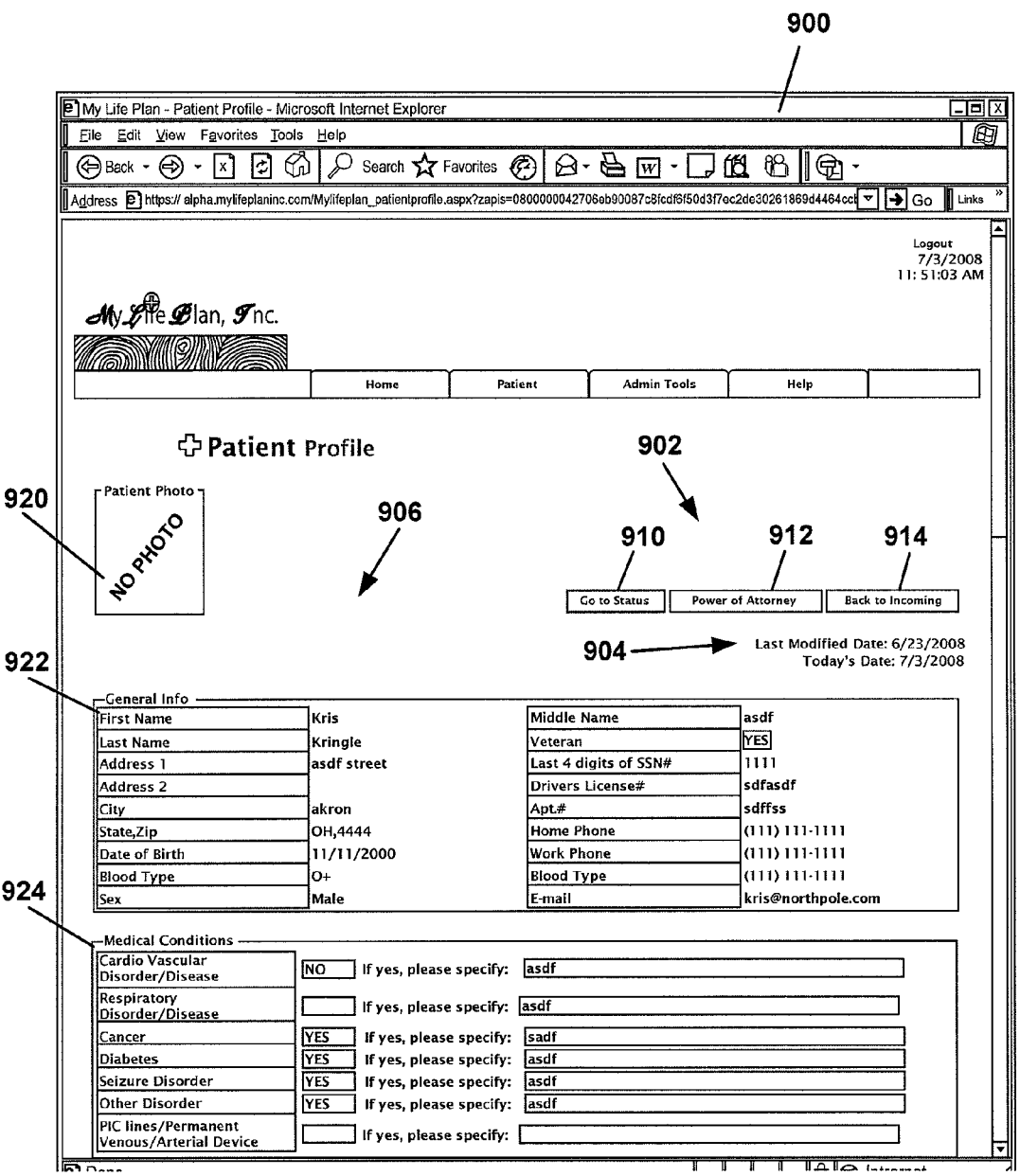
FIG. 9 is a screen shot of an exemplary patient profile interface according to the present disclosure.

FIG. 9 is a screen shot of an exemplary patient profile interface 900. Patient profile interface 900 includes navigational buttons 902, status display 904, and patient profile 906.

Navigational buttons 902 include Go To Status button 910, Power of Attorney button 912, and Back to Incoming button 914. Patient profile 906 includes photo section 920, general info section 922, and medical conditions section 924.

Patient profile interface 900 is an interface that provides information regarding a particular patient. In some embodiments the information includes data from patient data 120, shown in FIG. 1.

Figure 10:
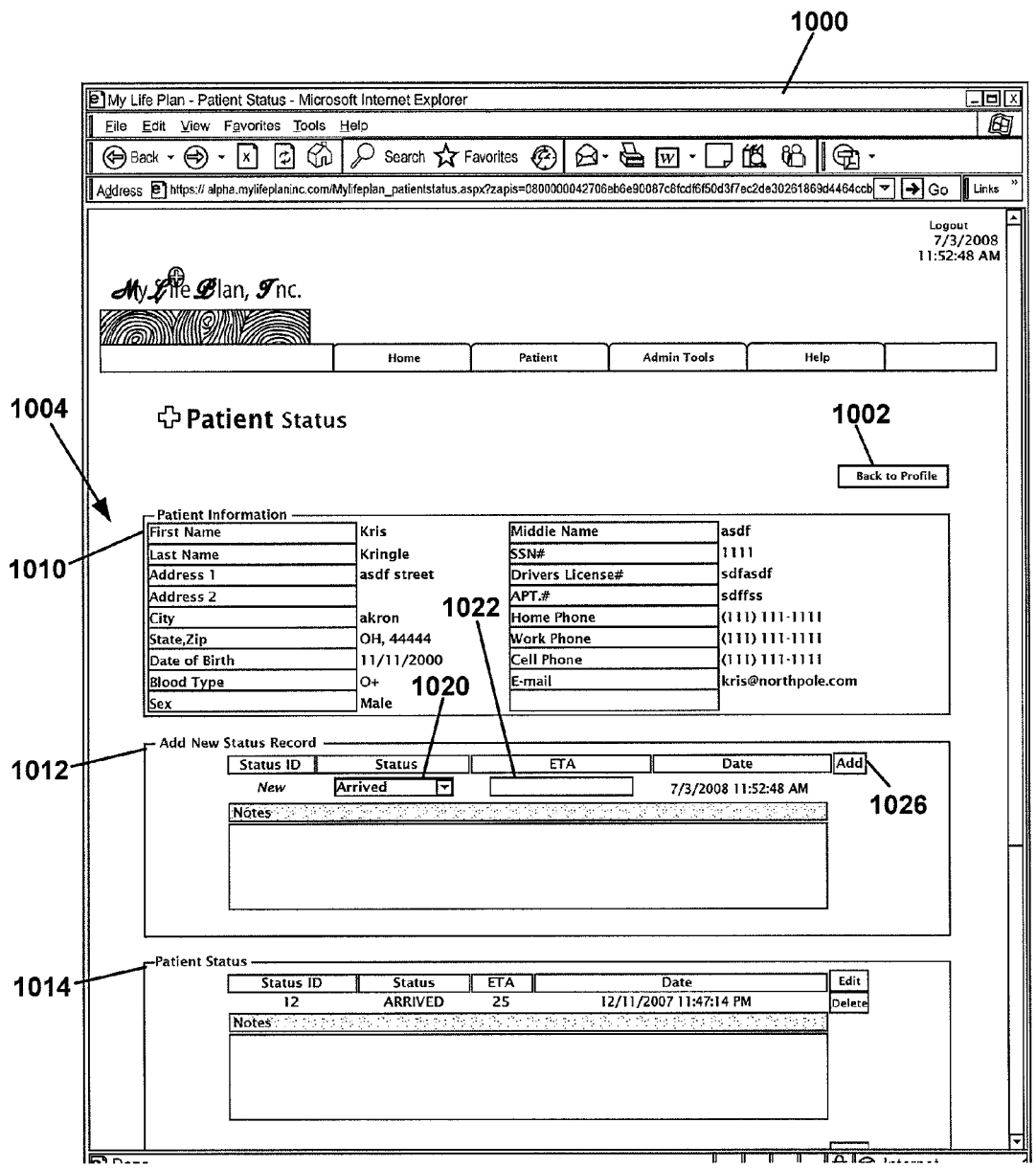
FIG. 10 is a screen shot of an exemplary patient status interface according to the present disclosure.
Figure 11:
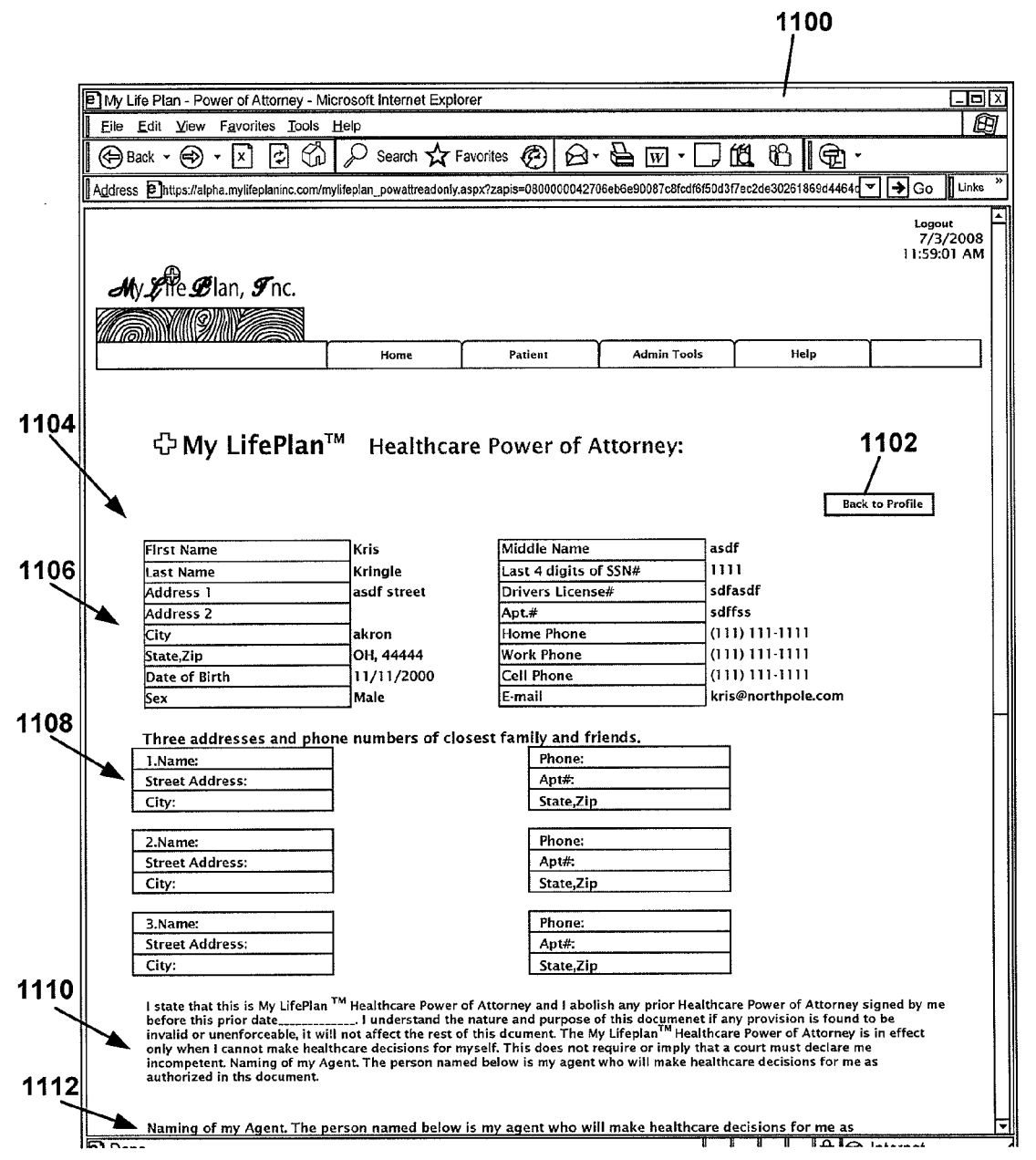

Navigational buttons 902 are selectable by a user to jump to a different interface display. When a user selects Go To Status button 910, a patient status interface (such as shown in FIG. 10) is displayed that is associated with the currently identified patient. When a user selects Power of Attorney button 912, a Power of Attorney interface is displayed. The Power of Attorney interface displays information regarding any Power of Attorney documents that have been executed by the patient. An example of a Power of Attorney interface is shown in FIG. 11. When Back to Incoming button 914 is selected, the Home interface 700 is again displayed, such as shown in FIGS. 7 and 8.

Patient profile 906 displays information about a patient. In some embodiments, patient profile 906 includes multiple sections, including photo section 920, general info section 922, and medical conditions section 924. Some embodiments include additional sections not visible in FIG. 9, such as pregnant section, other wishes section, emergency contact information section, primary physician section, health insurance section, and detailed patient status section.

Photo section 920 includes a photograph of the patient, if available. If no photo is available for a particular patient an image is displayed that so indicates. General info section 922 displays general information about the patient. Examples of general information include first name, last name, address 1, address 2, city, state, zip code, date of birth, blood type, gender, middle name, veteran status, social security number, drivers license number, apartment number, home telephone number, work telephone number, cell phone number, and e-mail address.

Medical conditions section 924 includes information regarding medical conditions of the patient. Examples of medical conditions that are displayed in medical conditions section 924 include cardio vascular disorder or disease, respiratory disorder or disease, cancer, diabetes, seizure disorder, other disorder, PIC lines or permanent venous or arterial devices, medical allergies, current medication (including prescription medication or over the counter medication), vision impairment, hearing impairment, and speech impairment. In some embodiments, medical conditions are associated with a YES or NO field that indicates whether or not the patient currently has or previously has had the condition, and includes a note field where further details regarding the condition are displayed.

Another possible section is a pregnant section that identifies whether or not the patient is currently pregnant, such as with a YES or NO field in the section. In some embodiments, the pregnant section also includes check boxes identifying special considerations relating to the pregnancy. For example, a first check box is associated with a statement "If I am pregnant and cannot speak for myself, I want all lifesaving procedures for myself, even if I am declared legally brain dead, if there is a chance that prolonging my life could allow my child to be born alive. My attorney-in-fact must honor this declaration." A second check box is associated with a statement "If I am pregnant and cannot speak for myself, I want any medical procedures that could prevent my death even if they could result in the death of my unborn child, provided all possible efforts are made to save the life of my unborn baby."

Another possible section is an Other Wishes section. In some embodiments the Other Wishes section is a text box that displays any other wishes that a patient would like made known to a caregiver during a health event.

Another possible section is an Emergency Contact Information section. This section displays information identifying who should be contacted upon an emergency. Examples of emergency contact information contained in this section include the contact information for one or more emergency contacts. For each contact, contact information includes contacts name, home telephone number, work telephone number, and cell phone number.

In some embodiments, the Emergency Contact Information section includes an automatic notification option. For example, each emergency contact includes an option for automatic emergency notification. If automatic emergency notification is selected, the system will automatically contact the person in the manner indicated upon the occurrence of a health event. For example, the system determines that a health event has occurred when the patient's status is set to In Transit, Arrived, or Patient Expired. In another embodiment, a health event is deemed to have occurred whenever a caregiver accesses the patient's profile. In yet another embodiment, a health event is deemed to have occurred whenever a caregiver (using a caregiver computing system) enters the patient's biometric identifier, such as by scanning the patient's fingerprint with the computing system. Once the system determines that a health event has occurred, the emergency contact(s) that have the automatic emergency notification feature enabled will be notified that a health event has occurred. Such notification can include an e-mail message, a text message, a telephone call with a voice message, a facsimile, or any other suitable communication. In some embodiments the notification is only a notification that a health event has occurred to the patient. In other embodiments, additional information is provided, such as the name and address of the caregiver facility that the patient is going to or being treated at, a description of the health event, a contact telephone number or web address where the emergency contact can get more information about the health event, or other information. In some embodiments, the emergency contact can access an emergency contact interface Web page that provides further information.

Some embodiments implement a Child Health Watch Program. In this program, system 100 (shown in FIG. 1) operates to store information about a child. Children are registered in the system by entering the child's name and other information. Examples of such information are described herein, and include medical history, and emergency contact information. In some embodiments, all students in a school or school district are registered. In other embodiments, all students of particular school programs or extracurricular activities are registered. In other embodiments, registration is voluntary and done individually by the child or the child's parents. Some embodiments include children who have a history of abuse, neglect, or being exploited. Other embodiments include children in foster care or adoption. Upon the occurrence of a health event, emergency, or other event, emergency responders are dispatched. The emergency responders access the child's records, such as by using a biometric identifier of the child or performing a keyword search for the record. The child's information is then immediately available for use by the emergency responder. In some embodiments, as soon as the emergency responder accesses the child's information, the system operates to contact an emergency contact (such as a parent) to alert the parent that the record has been accessed by an emergency responder or other caregiver. Some embodiments provide the same program for adults or people of all ages.

Some embodiments are also used for routine medical care. For example, people that are transitory often do not see the same caregiver for long, and instead move between caregivers. In the process, medical records are often lost or unavailable to a subsequent caregiver. As a result, the system described herein is used in some embodiments to provide a central repository for patient data, such that regardless of where the patient is or what caregiver is providing the care, the same patient information is always available.

Another possible section is a Primary Caregiver section. The Primary Physician section displays information about the primary caregiver. Examples of information about the primary caregiver include the caregiver's name, direct telephone number, facility name, and facility telephone number.

Another possible section is a Health Insurance section that displays information about the patient's health care coverage. Examples of health care information include provider name, provider telephone number, name of policy holder, and policy number.

Another possible section is a Patient Status section that displays information regarding the patient's status. An example of a Patient Status section is included in the Patient Status interface, shown in FIG. 10.

Another possible section is a Special Care Instructions section that displays information regarding the patient's desires for care upon the occurrence of a health event. In one example, Special Care Instructions includes a list of possible special care instructions associated with a YES or a NO. A YES indicates that the patient does want the caregiver to follow the associated Special Care Instruction and NO indicates that the patient does not want the caregiver to follow the associated Special Care Instruction. Examples of Special Care Instructions include do not resuscitate, do not intubate, do not resuscitate comfort care only, full code, cardiac resuscitation, medication for pain only to the extent that it would not seriously threaten to shorten my life, intubation/ventilators, hydration/IV tube, feeding tube, medication/treatment/hospitalization as needed.

Another possible section is an Organ Donor section that identifies whether or not particular organs should be donated upon death of the patient. Examples of organs include liver, heart valves, kidneys, skin/tissue, pancreas, bone/ligament, heart, veins, lungs, and eyes.

Another possible section is a Legal Acceptances section that identifies legal items for consideration by a caregiver. Examples include various statements. One possible statement is "I state that this is my Advance Directive Packet housed and distributed by Company A and that I am of sound mind and not under or subject to duress, fraud, or undue influence." Another possible statement is "I am a competent adult who understands and accepts the consequences of this action." Another possible statement is "These choices given above are to be implemented in the event that I am unable to give directives pertaining to my health care." Another possible statement is "I wish this Advance Directive Packet Declaration to be honored by my family and physicians as the final expression of my legal right to request or refuse healthcare.

In some embodiments, patient profile interface 900 is not only a display that provides information about a patient, but also receives information from a user to update the patient's profile. For example, the patient logs into the system through patient computing system 110 (shown in FIG. 1) and accesses patient profile interface 900. The patient then enters or edits the information as needed. Alternatively, data may only be edited by an administrator in some embodiments. For example, a patient communicates with the administrator and the administrator makes changes to the patient profile as needed. A benefit of this is that the administrator can act to ensure that information is not improperly changed for added security. In some embodiments a caregiver is allowed to edit and modify information in the patient profile.

More or less information is included in patient profile interface 900 in some embodiments.

Some embodiments include a method of entering patient information. The method includes hosting a seminar for participating users. The seminar provides educational information to the users to educate users about their choices and counsel clients through the completion of predefined forms, which may be arranged into a single packet. The seminar also includes taking of a photograph, reading a biometric identifier (such as fingerprinting the user), and notarizing any legal documents. In some embodiments an Attorney is available for consultation. In some embodiments the user signs a HIPPA compliant form that authorizes the data to be stored and communicated via electronic form, such as via a Web site. In some embodiments a corporate seal is applied to the completed packet to verify authenticity and legality. After the patient information has been gathered, it is entered into a database, either manually or via an automated process, such as by scanning the forms and optically recognizing the data entered into the forms.

FIG. 10 is a screen shot of an exemplary patient status interface 1000. Patient status interface 1000 displays information regarding the status of a patient and includes navigation button 1002 and patient status display 1004. Patient status display 1004 includes patient information section 1010, add new status record section 1012, and patient status section 1014. Add new status record section 1012 includes status prompt 1020, estimated time of arrival prompt 1022, notes field 1024, and add button 1026. Patient status section 1014 includes patient status display 1030, edit button 1032, and delete button 1034.

In this example, navigation button 1002 is a Back To Profile button. When the navigation button 1002 is selected by a user, the Patient Profile interface associated with the patient is again displayed, such as shown in FIG. 9.

Patient status display 1004 displays information regarding the status of the patient. In some embodiments the information is divided into multiple sections. In this example, patient status display 1004 includes patient information section 1010, Add New Status Record section 1012, and Patient Status section 1014.

Patient information section 1010 displays general information about the patient. An example of general information is described with reference to FIG. 9 above. More or less information about the patient can be displayed here as desired.

Add new status record section 1012 is a section where a caregiver can enter a new status record regarding the patient. In this example, add new status record section 1012 includes a status prompt 1020, an estimate time of arrival prompt 1022, notes field 1024, and add button 1026. Status prompt 1020 includes a pull down menu that allows a user to identify the current status of the patient as Arrived, Cancelled, In Transit, or Patient Expired, for example. If the status is In Transit, then Estimated Time of Arrival (ETA) prompt 1022 is provided for the caregiver to enter the estimated time of arrival of the patient. In some embodiments ETA is computed automatically based upon the position of the patient in an emergency vehicle. For example, a global positioning system (GPS) tracks the position of the emergency vehicle relative to the caregiver facility. The estimated transit time between the current position and the caregiver facility is computed as the ETA. Notes field 1024 is provided for a caregiver to enter notes regarding the current status of the patient.

Once the current status has been identified by a caregiver, the caregiver selects Add button 1026. The status is then updated in the system, and displayed in patient status section 1014.

Patient status section 1014 identifies the current status of the patient and includes patient status display 1030, edit button 1032, and delete button 1034. Patient status display 1030 shows the patients current status. For example, the current status is displayed with a status ID number (e.g., 12), a status identifier (e.g., Arrived), an ETA (e.g., 25), and a date and time that the status was last updated (e.g., Dec. 11, 2007 11:47:14 PM).

In some embodiments the patient's status includes additional information, such as the particular room number of the patient, the location of the patient at the present time (e.g., surgery in operating room B), or other information.

A caregiver can update the patient's status using Edit or Delete buttons 1032 and 1034. Upon selection of Edit button 1032, the caregiver is allowed to update the patient's status. If the caregiver wants to delete a status entry, delete button 1034 is selected. The updated status information is then stored by the server.

FIG. 11 is a screen shot of an exemplary Power of Attorney interface 1100. Power of Attorney interface 1100 includes navigation button 1102 and Power of Attorney information 1104. Power of Attorney information 1104 includes multiple sections, such as general information section 1106, family or friends information section 1108, Power of Attorney statement section 1110, and naming of agent section 1112.

In this embodiment, navigation button 1102 is a Back to Profile button that, when selected by a user, returns to the Patient profile interface, such as shown in FIG. 9.

As noted above, Power of Attorney information 1104 includes multiple sections, such as general information section 1106, family or friends information section 1108, Power of Attorney statement section 1110, and naming of agent section 1112.

Patient information section 1106 displays general information about the patient. An example of general information is described with reference to FIG. 9 above. More or less information about the patient can be displayed here is desired.

Family or friends information section 1108 displays contact information for some of the patient's closest family or friends. Examples of contact information include the names, addresses, and telephone numbers of the contacts.

Power of Attorney statement section 1110 includes a statement regarding power of attorney. An example statement is "I state that this is my Healthcare Power of Attorney and I abolish ant prior Healthcare Power of Attorney signed by me before this prior date. I understand the nature and purpose of this document. If any provision is found to be invalid or unenforceable, it will not affect the rest of this document. This healthcare power-of-attorney is in effect only when I cannot make health care decisions for myself. This does not require or imply that a court must declare me incompetent."

Naming of agent section 1112 is a section that identifies the agent will have the power of attorney identified in the power of attorney statement section 1110. Naming of agent section 1112 includes a statement such as the following "The person named below is my agent will make health care decisions for me as authorized in this document." This section also includes an identification of the agent, such as including the agent's name, address, and telephone number.

Another possible section is an alternate agent section. The alternate agent section identifies one or more alternate agents who will be given the power of attorney identified in power of attorney statement section 1110 in the event that the agent named in the naming of agent section 1112 is unable to perform. In some embodiments, the alternate agent section includes a first alternate agent and a second alternate agent. The agents are identified by the name, address, and telephone number, for example. In addition, the alternate agent section can include a statement such as the following: "Any persons can rely on a statement by any alternate agent named above that he or she is properly acting under this document and such person does not have to make any further investigation or inquiry."

Another possible section is an additional instructions or limitations section. Additional instructions can include, for example, contact information for who the person named as power of attorney should contact, such as a first contact and a second contact, to inform the contacts that the agent is going to act on the power of attorney. Additional instructions or limitations can be manually provided into a text box in some embodiments.

FIG. 12 is a screen shot of an exemplary patient search interface 1200. The patient search interface allows a search to be performed to locate patient records matching search criteria. Patient search interface 1200 includes search fields 1202, search by print button 1204, and search results 1206.

Search fields 1202 include last name prompt 1210, patient ID prompt 1212, social security prompt 1214, and search button 1216, for example. Last name prompt 1210 is a field where a user enters a last name or part of a last name to be searched. Patient ID prompt 1212 is a field where a user enters a patient identification number or part of the identification number to be searched. Social security prompt 1214 is a field where a user enters a social security number or part of a social security number (such as the last four digits) to be searched. A user can enter search criteria into one or more of the search fields 1202 and then click search button 1216 to search the patient records. The search criteria are then used by the server to search through the patient records to find those records that match the search criteria. The results are displayed in search results 1206.

Search by print button 1204 is selected by a user to initiate a search by a biometric identifier, such as a fingerprint. Upon selection of search by print button 1204, a biometric reader is activated to read the biometric identifier. When the biometric identifier is received, the server uses the identifier to search for the matching patient record.

After a search has been performed based on the search criteria provided in search fields or based on the biometric identifier of the patient, the search results 1206 are displayed. In the illustrated example, a search has been performed for any patients that have a last name beginning with "Duck." Two matching patients are listed, including Donald Duck and Daffy Duck. The patient name of each matching record is a hyperlink that can be selected by a user to bring the user to the patient profile interface associated with the patient.

FIG. 13 is a screen shot of an exemplary client search interface 1300. Some embodiments include a client search interface 1300 in addition to the Patient Search interface shown in FIG. 12. The client search interface 1300 is typically used by an administrator rather than a caregiver. Client search interface 1300 includes search fields 1302 and search results 1304.

Search fields 1302 include last name prompt 1310, patient ID prompt 1312, social security prompt 1314, and search button 1316, for example. Last name prompt 1310 is a field where a user enters a last name or part of a last name to be searched. Patient ID prompt 1312 is a field where a user enters a patient identification number or part of the identification number to be searched. Social security prompt 1314 is a field where a user enters a social security number or part of a social security number (such as the last four digits) to be searched. A user can enter search criteria into one or more of the search fields 1302 and then click search button 1316 to search the patient records. The search criteria are then used by the server to search through the patient records to find those records that match the search criteria. The results are displayed in search results 1304.

Search results 1304 displays the list of records that match the search criteria. In some embodiments each search result includes a patient ID number 1320, registered biometric identifier link 1322, edit profile link 1324, patient records link 1326, patient name 1328, telephone number 1330, and social security number 1332.

Figure 15:
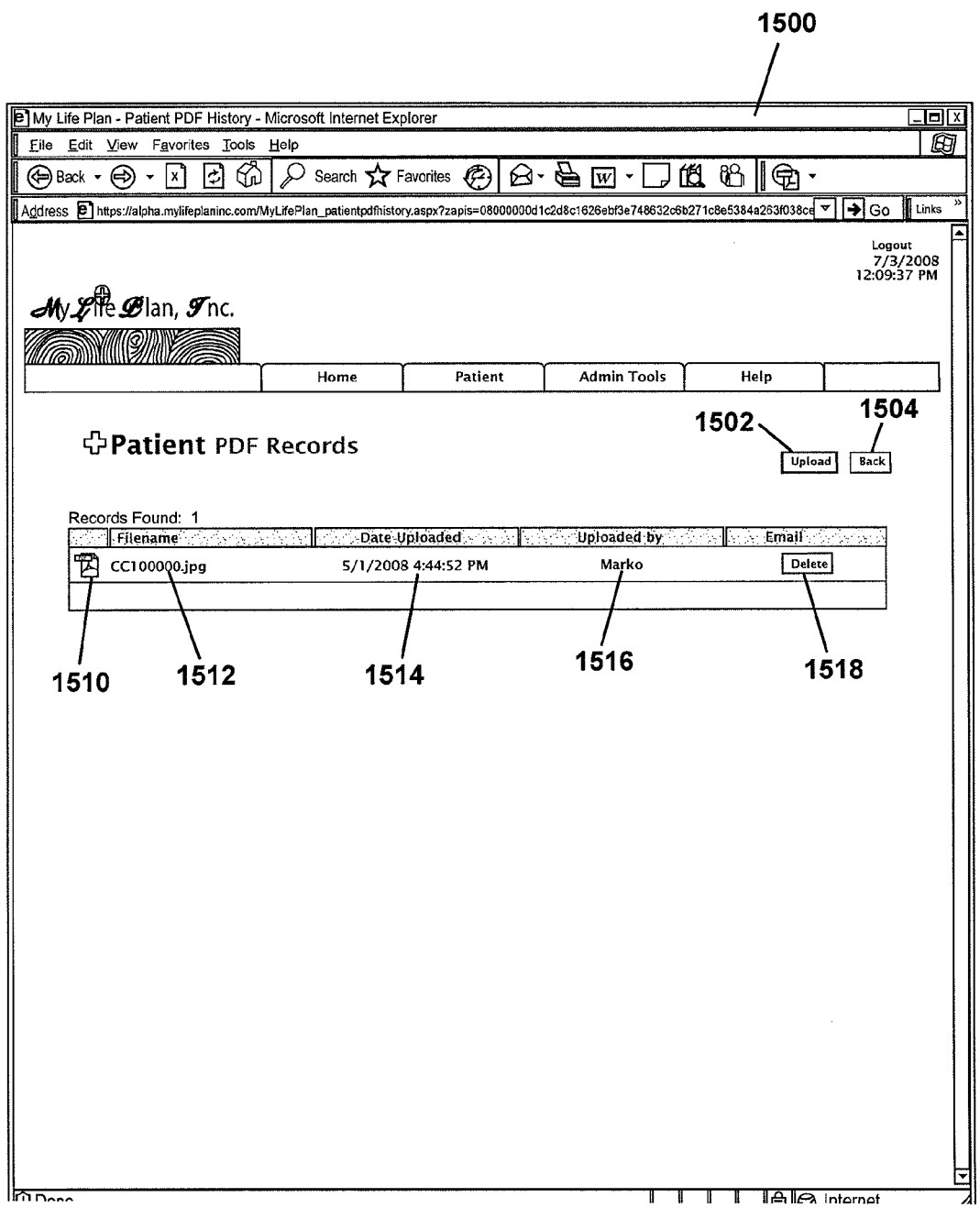
FIG. 15 is a screen shot of an exemplary patient records interface according to the present disclosure.

Registered biometric identifier link is selectable by a user to navigate to a biometric identifier interface screen where the biometric identification information may be reviewed or updated, such as to re-scan a biometric identifier. Edit profile link is selectable by a user to navigate to a client profile interface, such as shown in FIG. 14, where the patient's information can be reviewed and updated as needed. The patient records link is selectable by a user to navigate to the patient records interface, such as shown in FIG. 15.

FIG. 14 is a screen shot of an exemplary client profile interface 1400. Client profile interface 1400 displays information associated with a patient. In some embodiments, client profile interface 1400 is designed for use by an administrator. Client profile interface 1400 includes buttons 1402 and profile information 1404. Buttons 1402 include Save/Update button 1410 and Power of Attorney button 1412. Profile information 1404 includes login information section 1420, general information section 1422, and emergency contact information section 1424.

Save/Update button 1410 is selectable by a user when updated information entered into the profile information 1404 should be saved. Upon selection of the Save/Update button 1410, profile information 1404 is stored to memory.

When Power of Attorney button 1412 is selected by a user the Power of Attorney interface (such as shown in FIG. 11) associated with the current patient is displayed.

As stated above, profile information 1404 includes login information section 1420, photo section 1421, general information section 1422, and emergency contact information 1424. Profile information 1404 can be viewed by the user or can be changed, if needed. If a change is made, the user then selects Save/Update button 1410.

Login information section 1420 displays various information associated with the user login process. Examples of such information include a username and password, a change password option, and an activate advanced directives option.

The change password option provides a safeguard against inadvertently changing the users password. In order to change the password, this option is first selected. Upon selection of this option, the password prompt is then unlocked so that the new password can be entered. The Save/Update button is then selected to store and lock the new password. In some embodiments the current password is not displayed in login information section 1420 unless the change password option is selected to provide added security.

The activate advanced directives option selects whether or not the patient account includes advanced directives. If so, advance directive options are enabled.

Photo section 1421 includes a photograph of the patient. The photograph can be selected or changed by choosing a Browse button and identifying the photograph file associated with the patient.

General information section 1422 displays general information about the patient, such as described above. Information can be changed or entered as needed.

Emergency contact information section 1424 provides information about who to contact in the event of an emergency. Emergency contact information can be changed or entered as needed.

Other sections can be included in client profile interface 1400 as desired. Examples of other sections are discussed above.

FIG. 15 is a screen shot of an exemplary patient records interface 1500 that displays a list of stored files that are associated with the patient. Stored files can include any format, such as Portable Document Format (PDF), WORD® document format, JPEG or other image format (including GIF, TIFF, etc.), or other file format. In some embodiments, the files include content that is related to health care. Examples include executed copies of documents, such as an advance directive, living will, power of attorney for health care, or other document. Non-health care specific documents can also be stored, such as a will or other record.

In this example, a single file is currently associated with the patient. To upload additional files, an upload button 1502 is provided. A back button 1504 is provided to return the user to the previous interface page, such as the client profile interface shown in FIG. 14.

A summary of each file stored in the system is displayed in patient records interface 1500. The summary includes, for example, link 1510 to the actual file, filename 1512, date and time 1514 that the file was uploaded, user ID 1516 of the user that uploaded the file, and delete button 1518 that can be used to delete the file.

FIG. 16 is a screen shot of an exemplary company profile interface 1600. Company profile interface includes information about a particular company. In this example, company profile interface 1600 includes company profile information 1602 and Save/Update button 1604. The company profile information 1602 includes information about the company, such as company name, address, telephone number, contract start and end dates, business type 1610, and primary contact information.

In some embodiments, business type 1610 is selected from hospital or doctor's office. Other embodiments include other company types, such as emergency medical responder, service provider, or other company types.

After the information has been entered or modified, the Save/Update button is selected to save the information.

FIG. 17 is an exemplary menu manager interface 1700. In some embodiments the menu manager interface 1700 is accessible from the home interface (shown in FIG. 7) by selecting menu manager from the administrative tools tab. Menu manager interface 1700 provides options to customize various interface screens. In some embodiments the menu manager interface 1700 is only available to an administrator.

In some embodiments menu manager interface 1700 operates to define access rights to various features and interfaces based upon a user role 1702. The user role 1702 is selected from a list of available user roles. Examples of user roles include system administrator, site administrator, company administrator, user, default, paramedic, hospital, and company representative.

For each user role 1702, a set of menus 1704 are available. Each menu 1704 is associated with a navigation tab, such as tabs 702 shown in FIG. 7. Each menu 1704 is associated with a set of submenus 1706. Each submenu is associated with an option of the list of options for the associated navigation tab.

An administrator can customize the list of menus and submenus that are available for a particular user role. To do so, buttons 1708 and 1710 are provided. Button 1708 is selectable to delete a selected menu and all of its submenus from the selected role. Button 1710 is selectable to delete a selected submenu from a menu.

Menu information is displayed in menu information section 1712. Submenu information is displayed in submenu information section 1714. Information includes the text of the menu or submenu and a Web address to the interface associated with the menu or submenu.

To update or change information in menu information section 1712 or submenu information section 1714, add or update menu section 1716 is provided.

Additional buttons are provided in some embodiments. Examples include Add as new menu to role button 1720, update selected menu button 1722, add as new submenu to selected menu 1724, and update selected submenu button 1726.

Sample menu display 1730 is provided to show a sample of the navigation tabs as currently defined in menu manager interface 1700.

FIG. 18 is a screen shot of an exemplary user search interface 1800 that is operable to search through user records to identify one or more user accounts. User search interface 1800 includes search fields 1802 and search results 1804.

Search fields 1802 include last name prompt 1810, user role prompt 1812, username prompt 1814, and search button 1816. The prompts receive input from a user to define search criteria. The search criteria are then used to perform a search when the user selects search button 1816.

The search is then performed, such as by the server, to identify the user records that match the search criteria. The results are displayed in search results 1804. In some embodiments each search result includes a status identifier, a profile check box, a username, a role, and an e-mail address. The username is a hyperlink to the user profile interface, shown in FIG. 19.

FIG. 19 is a screen shot of an exemplary user profile interface 1900 that displays user information and allows the user information to be updated as needed. User profile interface 1900 includes Save/Update button 1902 and user information 1904.

After user information has been entered or modified, Save/Update button 1902 is selected by a user to store the user information.

User information 1904 includes associations section 1906, photo section 1908, login information section 1910, contact information section 1912, and fingerprint registration section 1914.

Associations section 1906 includes information such as active status (active or inactive), title, company name, office ID, and employee ID.

Photo section 1908 includes a photograph of the user, and includes a Browse button, which when selected allows a user to locate a photo file. The photo is then associated with the user profile and displayed in photo section 1908.

Login information section 1910 includes information such as login name, display as, member of (such as: system admin, site admin, company admin, paramedic, hospital, or company representative), and login password. A change password option is provided to change the login password.

Contact information section 1912 includes first name, last name, address, start of service date, telephone number, cell phone number, fax number, and e-mail address.

Fingerprint registration section 1914 includes a register fingerprint (or other biometric identifier) option. If the user selects the register fingerprint option, the user is prompted to enter a biometric identifier, such as by placing a finger against a fingerprint reader or using another biometric reader. The fingerprint reader scans the fingerprint. This biometric identifier is then stored as associated with the user profile.

FIG. 20 is a screen shot of an exemplary user log interface 2000 that allows a user to search for and review a user log. User log interface 2000 includes search fields 2002, search button 2004, and search results 2006. User log interface 2000 is accessible, for example, by selecting a track users option from the administrative tools tab 714, such as shown in FIG. 7. In some embodiments user log interface 2000 is only accessible to an administrator.

Search fields 2002 allow a user to enter search criteria, such as start date, end date, first name, and last name. After entering the desired search criteria, a search button 2004 is selected to perform a search of the user log for entries that match the search criteria. In some embodiments the user log is maintained in a database of the server.

The user log entries that match the search criteria are displayed in search results 2006. In some embodiments, a summary of each user log entry is displayed. The summary includes logon date, logoff date, username, first name, last name, and IP address.

FIG. 21 is a screen shot of an exemplary track changes interface 2100 that allows a user to review changes made to system records, including patient or client information. In some embodiments the server maintains a log of changes that is searchable using track changes interface 2100. Track changes interface includes search fields 2102, search button 2104, and search results 2106. In some embodiments track changes interface 2100 is only accessible to an administrator.

Search fields 2102 allow a user to enter search criteria, such as a start date, end date, first name, last name, and username. After the search criteria have been entered, a search button 2104 is selected by the user. A search of the log of changes is then performed.

Search results 2106 displays the list of entries that match the search criteria. In some embodiments a summary of each entry is displayed. The summary includes a number, username, first name, last name, table, column, page, control, previous value, new value, key name, key value, and date and time when the change was made.

This information allows an administrator to review all changes that were made, and if necessary, to undo changes that were made. For example, if it is found that an unauthorized access has occurred, the changes made during the unauthorized access can be reversed by the administrator by reviewing the changes that were made by the user during the period of unauthorized access.

FIG. 22 is a screen shot of an exemplary manage roles interface 2200 through which a user can manage user roles. In some embodiments, manage roles interface 2200 is accessible by selecting manage roles from the administrative tools tab 714, shown in FIG. 7. Manage roles interface 2200 includes load new pages section 2202, create new role section 2204, assign pages to role section 2206, add/remove pages section 2208, and assign pages display section 2210.

Load new pages section 2202 includes a button that is selectable by a user to request that new pages be loaded. Upon selection of the button, the system operates to load new pages.

Create new role section 2204 includes a field for identifying a name for a new role and a button for saving the new role.

After a new role is defined with create new role section 2204, pages can be assigned to the role using assign pages to role section 2206 and add/remove pages section 2208. In assign pages to role section 2206 the user selects a role. The user then selects a page to add or remove from that role in add/remove pages section 2208. To remove a role altogether, the role is selected and a remove role button is selected in role section 2206. To remove a page, the remove page button is selected in section 2208. To add a page, the add page button is selected in section 2208. To set a page to the default page for a role, the set to page button is selected in section 2208.

After selecting a particular role in assign pages to role section 2206, the pages assigned to that user role are displayed in assign pages display section 2210. In some embodiments, assign pages display section 2210 includes a rule name and a page name.

FIG. 23 is a screen shot of an exemplary print forms interface 2300. In some embodiments, print forms interface 2300 is accessible by selecting the print forms option of help tab 716, shown in FIG. 7. Print forms interface 2300 includes links 2302 that are associated with various forms. Examples of forms include terms of use, a HIPPA release, a disclaimer, an advanced directive, and a certification of DNR/DNI. Other forms may also be included, as desired. Selection of one of links 2302 opens the identified document so that the user can review the document or send the document to a printer.

Figure 24:
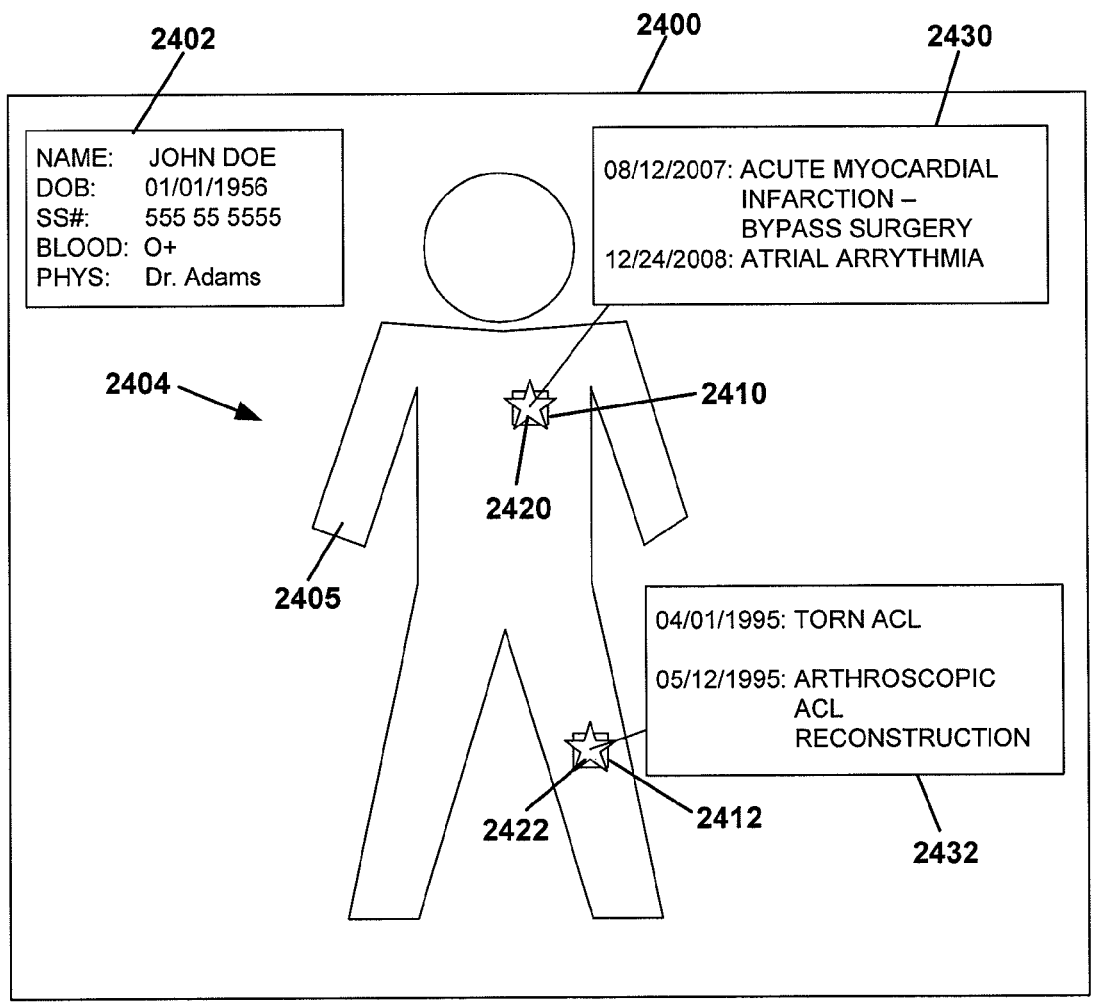
FIG. 24 is a screen shot of an exemplary health history interface according to the present disclosure.

FIG. 24 is a screen shot of an exemplary health history interface 2400. The health history interface 2400 provides information graphically regarding the health history of a patient. In some embodiments, health history interface 2400 includes a general information section 2402, and graphical body representation section 2404. Graphical body representation section 2404 includes body parts 2410 and 2412, history flags 2420 and 2422, and history summaries 2430 and 2432.

In some embodiments, health related information regarding a patient is displayed graphically through health history interface 2400 to provide a convenient interface for reviewing the health history of a patient.

General information section 2402 provides general information about the patient, such as the patient's name, date of birth, social security number, blood type, and primary physician. More or less information can be included in general information section 2402.

Graphical body representation section 2404 includes a graphical representation of a human body 2405 or body part (s) 2420 and 2422. In this example, the body 2405 includes a heart 2410 organ and a knee 2412 joint. If the patient has a history of health problems with a particular body part, history flags 2420 and 2422 are displayed for the respective body part. For example, history flag 2420 is associated with heart 2410 organ and history flag 2422 is associated with knee 2412 joint.

If a user desires to view more information about a particular body part, the user selects the respective history flag 2420 or 2420, such as by moving a mouse cursor over the history flag or by clicking on the history flag. When history flag 2420 is selected, history summary 2430 is displayed to show a summary of health information associated with body part 2410. In some embodiments the history summary 2430 identifies a date of a health event, and a brief description of the health event, and a brief description of the treatment provided for the health event. For example, "Aug. 12, 2007: Acute myocardial infarction—bypass surgery." In some embodiments more or less information is provided in the history summary, such as the date and a brief description of the health event: "Dec. 24, 2008: atrial arrhythmia." Similarly, when history flag 2422 is selected, history summary 2432 is displayed to show a summary of health information associated with body part 2412. One example of history summary 2432 is "Apr. 1, 1995: torn ACL," and "May 12, 1995: arthroscopic ACL reconstruction." In some embodiments, the user can select a history flag 2420 or 2422 or a health summary 2430 or 2432 to be taken to a patient profile interface (or other patient information interface) to obtain more information about the health history.

In some embodiments, upon selection of a body part, such as heart 2410 organ or knee 2412 joint, a keyword search is initiated to search through the records associated with the patient to identify records including the keyword, such as "knee." The results are then provided in a history summary, such as summary 2430, or listed on a separate interface screen. In some embodiments, patient records include an anatomy field or set of fields in which a body part or parts are associated with particular health records. The search involves a search of the anatomy field or set of fields in some embodiments.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A health care data management system comprising a server device including a processor device and at least one computer storage medium, the at least one computer storage medium storing a database and data instructions, wherein the data instructions are executable by the processor device to:
   register a user with the server device by receiving user data including a first biometric identifier through a web interface;
   store the user data and the first biometric identifier in the database at the server device, the server device and the database being configured to operate remote from the user;
   associate the first biometric identifier with the user data in the database;
   receive health care information pertaining to the user and store the health care information in the user data in the database;
   receive from an emergency vehicle computing system a request including a second biometric identifier;
   search the database with the server device to identify the first biometric identifier as a match to the second biometric identifier;
   transmit at least part of the user data associated with the first biometric identifier to the emergency vehicle computing system in response to the request;
   update a status of the user in the user data of the database to indicate that the user is in transit to the medical care facility;
   receive login information from a caregiver computing device at the medical care facility;
   conduct a search of the user data in the database to identify patient records having user data that indicates that the associated user is in transit to the medical care facility; and
   transmit web page data to the caregiver computing device at the medical care facility to generate and display to a caregiver a total number of incoming patients and a list of the incoming patients, the list identifying, for each identified patient record: the name of the patient that is in transit, an estimated time that the patient will arrive at the medical facility, and a notes field identifying the current medical status of the patient.

2. The health care data management system of claim 1, wherein the server further comprises a web server, and wherein transmitting the at least part of the user data is performed by sending data defining a web page.

3. The health care data management system of claim 1, wherein the emergency vehicle computing device is communicatively coupled to a biometric reader and configured to communicate with the server across a data communication network, wherein the emergency vehicle computing device reads the second biometric identifier from the user and sends the request including the second biometric identifier to the server.

4. The health care data management system of claim 3, wherein the emergency vehicle computing device is a mobile computing device used by a caregiver, a police officer, an emergency responder, or a military unit.

5. The health care data management system of claim 1, further comprising a patient computing device configured to communicate with the server across a data communication network, wherein the instructions are further executable by the processor to:
   receive a request from the patient computing device requesting at least part of the user data;
   send to the patient computing device the at least part of the user data;
   receive updated user data from the patient computing device; and
   store the updated user data in place of the user data.

6. The health care data management system of claim 1, wherein receiving health care information pertaining to the user comprises receiving health care information from the caregiver computing system.

7. The health care data management system of claim 1, wherein user data includes at least some of the following: physician notes, electronic medical records, immunization records, surgical history, medication records, medical treatment records, identification of medical allergies, obstetric history, habit history, family medical history, mental health history, employment history, travel history, family history, common activities, advance directive, living will, and power of attorney for health care.

8. The health care data management system of claim 1, wherein the instructions executable to receive from the caregiver the request including the second biometric identifier are further executable to:
   receive a scanned fingerprint of the registered user from a fingerprint scanner to generate the second biometric identifier at the emergency vehicle computing system; and
   send the request including the second biometric identifier from the emergency vehicle computing system to the server.

9. A method of providing health care data to an emergency caregiver computing device, the method comprising:
   registering a user by receiving user data through a web interface provided by a web server device, the web interface including a plurality of web pages, wherein at least one of the web pages prompts for a first biometric identifier;
   receiving and storing the user data and the first biometric identifier in a database accessible by the web server device and associating the first biometric identifier with the user data in the database, the database being remote from the user;

receiving health care information through the web interface, the health care information pertaining to the user, and storing the user data in the database with the web server device;

sending web page data to an emergency vehicle computing system to generate a patient search page, the patient search page including a selectable control to initiate a search for a patient using a biometric identifier;

receiving from the emergency vehicle computing system through the web interface a search request including a second biometric identifier, the second biometric identifier generated by a biometric reader coupled to the emergency vehicle computing device;

searching the database with the web server device to identify the first biometric identifier as a match to the second biometric identifier;

identifying a record associated with the first biometric identifier;

sending web page data to the emergency vehicle computing system to generate a patient search results page, the patient search results page displaying at least a patient name and a selectable link associated with the record;

after receiving a selection of the selectable link, sending web page data to the emergency vehicle computing system to generate at least one patient records page, the at least one patient records page including at least part of the user data associated with the first biometric identifier from the record;

updating a status of the patient in the patient's record in the database to indicate that the patient is in transit to a medical care facility and to provide a current medical status of the patient;

receiving login information from a caregiver computing device at the medical care facility;

evaluating the login information and determining that the login information is associated with an active user account associated with the caregiver;

conducting a search of the patient records to identify patient records that indicate that the associated patient is in transit to the medical care facility; and sending web page data to the caregiver computing device at the medical care facility to generate and display to the caregiver a total number of incoming patients and a list of the incoming patients, the list identifying, for each identified patient record:
  the name of the patient that is in transit,
  an estimated time that the patient will arrive at the medical care facility, and
  a notes field identifying the current medical status of the patient.

10. The method of claim 9, wherein registering a user comprises assigning a user role to the user, the user role selected from at least a patient role, an administrator role, and a caregiver role, wherein the assigned user role is subsequently used by the web server to selectively provide information to the user based on the user role.

11. The method of claim 9, wherein the patient search results page includes a list of records that match the search query, wherein each record identified in the list includes on the patient search results page an associated patient ID number, registered biometric identifier link, edit profile link, the patient records link, patient name, telephone number, and a social security number for that record, wherein the registered biometric identifier link is selectable to navigate to a biometric identifier interface screen where the biometric identification information may be reviewed or updated for that record, wherein the edit profile link is selectable to navigate to a client profile interface page.

* * * * *